(12) United States Patent
Bruchez et al.

(10) Patent No.: US 6,274,323 B1
(45) Date of Patent: Aug. 14, 2001

(54) METHOD OF DETECTING AN ANALYTE IN A SAMPLE USING SEMICONDUCTOR NANOCRYSTALS AS A DETECTABLE LABEL

(75) Inventors: Marcel P. Bruchez, Union City; R. Hugh Daniels, Palo Alto; Stephen A. Empedocles, Mountain View; Vince E. Phillips, Sunnyvale; Edith Y. Wong, Danville; Donald A. Zehnder, San Carlos, all of CA (US)

(73) Assignee: Quantum Dot Corporation, Palo Alto, CA (US)

( * ) Notice: Subject to any disclaimer, the term of this patent is extended or adjusted under 35 U.S.C. 154(b) by 0 days.

(21) Appl. No.: 09/566,014

(22) Filed: May 5, 2000

Related U.S. Application Data
(60) Provisional application No. 60/133,084, filed on May 7, 1999.

(51) Int. Cl.$^7$ .............................. C12Q 1/68; G01N 1/30
(52) U.S. Cl. .................................. 435/6; 250/307
(58) Field of Search .............................. 435/6, 7.92, 7.93

(56) References Cited

U.S. PATENT DOCUMENTS

| | | | |
|---|---|---|---|
| 5,505,928 | 4/1996 | Alivisatos et al. | 423/299 |
| 5,665,582 | * 9/1997 | Kausch et al. | 435/181 |
| 5,674,698 | * 10/1997 | Zarling et al. | 435/7.92 |
| 5,690,807 | 11/1997 | Clark, Jr. et al. | 205/655 |
| 5,739,001 | * 4/1998 | Brown et al. | 435/7.93 |
| 5,861,279 | * 1/1999 | Zhang et al. | 435/69.1 |
| 5,990,479 | 11/1999 | Weiss et al. | 250/307 |

FOREIGN PATENT DOCUMENTS

| | | |
|---|---|---|
| WO 98/04740 | 2/1998 | (WO) . |
| WO 99/26299 | 5/1999 | (WO) . |
| WO 00/17642 | 3/2000 | (WO) . |
| WO 00/17655 | 3/2000 | (WO) . |

OTHER PUBLICATIONS

Kenan, D.J. et al., "Exploring molecular diversity with combinatorial shape libraries", Trends in Biochemical Sciences, vol. 19, pp. 57–64 (1994).*

Dabbousi et al., "(CDSE) ZNS Core–Shell Quantum Dots: Synthesis and Characterizations of a Size Series of Highly Luminescent Nanocrystallites," *Journal of Physical Chem. B* 101(46):9463–9475. XP–002095418 (1997).

Lacoste et al., "Super Resolution Molecular Ruler Using Single Quantum Dots," *Biophysical Journal* 78:402A, XP000933548 (2000).

Bruchez, Jr., et al., "Semiconductor Nanocrystals as Fluorescent Biological Labels," *Science* 281:2013–2016 (1998).

Bruchez, Marcel Pierre, Jr., "Luminescent Semiconductor Nanocrystals: Intermittent Behavior and Use as Fluorescent Biological Probes," *UMI Dissertation Information Service* pp. 1–115 (1998).

Chan et al., "Quantum Dot Bioconjugates for Ultrasensitive Nonisotopic Detection," *Science* 281:2016–2018 (1998).

Heiskanen et al., "Visual Mapping by Fiber–FISH," *Genomics* 30:31–36 (1995).

Heiskanen et al., "High Resolution Mapping Using Fluorescence In Situ Hybridization to Extended DNA Fibers Prepared From Agarose–Embedded Cells," *BioTechniques* 17(5):928–933 (1994).

Kitadai et al., "Multiparametric in Situ Messenger RNA Hybridization Analysis to Detect Metastasis–Related Genes in Surgical Specimens of Human Colon Carcinomas," *Clinical Cancer Research* 1:1095–1102 (1995).

Macville et al., "Spectral Karyotyping, a 24–Colour FISH Technique for the Identification of Chromosomal Rearrangement," *Histochem Cell Biol.* 108:299–305 (1997).

Meltzer et al., "Rapid Generation of Region Specific Probes by Chromosome Microdissection and Their Application," *Nature Genetics* 1:24–28 (1992).

Nath et al., "Fluorescence in Situ Hybridization (FISH): DNA Probe Production and Hybridization Criteria," *Biotechnic & Histochemistry* 73(1):6–22 (1997).

Raap, Anton K., "Advances in Fluorescence in Situ Hybridization," *Mutation Research* 400:287–298 (1998).

Schröck et al., "Multicolor Spectral Karyotyping of Human Chromosomes," *Science* 273:494–497 (1996).

Speel et al., "Improved mRNA in Situ Hybridization on Formaldehyde–Fixed and Paraffin–Embedded Tissue Using Signal Amplification With Different Haptenized Tyramides," *Histochem Cell Biol.* 110:571–577 (1998).

Swiger et al., "Fluorescence in Situ Hybridization: A Brief Review," *Environmental and Molecular Mutagenesis* 27:245–254 (1996).

* cited by examiner

*Primary Examiner*—Kenneth R. Horlick
*Assistant Examiner*—Teresa Strzelecka
(74) *Attorney, Agent, or Firm*—Robins & Pasternak LLP

(57) ABSTRACT

The use of semiconductor nanocrystals as detectable labels in various chemical and biological applications is disclosed. The methods find use for detecting a single analyte, as well as multiple analytes by using more than one semiconductor nanocrystal as a detectable label, each of which emits at a distinct wavelength.

40 Claims, 6 Drawing Sheets

|        |   | A | B | C |
|--------|---|---|---|---|
| 0 nM   | 1 | O | O | O |
| 1 nM   | 2 | O | O | O |
| 10 nM  | 3 | O | O | O |
| 100 nM | 4 | O | O | O |
| 1 uM   | 5 | O | O | O |
| 10 uM  | 6 | O | O | O |
| 100uM  | 7 | O | O | O |
| 1 mM   | 8 | O | O | O |

A1-A8, IL-1 5000 beads each

B1-B8, IL-5 2500 beads IL-1 2500 beads each

C1-C8, IL-5 5000 beads each

ALL: 50 ul total volume

*FIG. 3*

METHOD OF DETECTING AN ANALYTE IN A SAMPLE USING SEMICONDUCTOR NANOCRYSTALS AS A DETECTABLE LABEL

CROSS-REFERENCE TO RELATED APPLICATION

This application is related to provisional patent application Ser. No. 60/133,084, filed May 7, 1999, from which priority is claimed under 35 USC §119(e)(1) and which is incorporated herein by reference in its entirety.

FIELD OF THE INVENTION

The present invention relates generally to the detection of analytes in a sample. In particular, the invention relates to assays that use semiconductor nanocrystals as a detectable label. The invention further relates to assays in which multiple analytes can be detected simultaneously by using more than one semiconductor nanocrystal as a detectable label, each of which emits at a distinct wavelength.

BACKGROUND OF THE INVENTION

A variety of chemical and biological assays exist to identify an analyte of interest in a given sample. For example, immunoassays, such as enzyme-linked immunosorbent assays (ELISAs) are used in numerous diagnostic, research and screening applications. In its most common form, an ELISA detects the presence and/or concentration of an analyte in a sample using an antibody which specifically recognizes the analyte. An enzyme label, capable of providing a detectable signal, is conjugated to the antibody. The analyte is either immobilized directly onto a solid support (direct-capture ELISA) or is bound to a different specific antibody which itself is immobilized on a solid support. The presence of the immobilized analyte is detected by binding to it the detectably labeled antibody. A variety of different ELISA formats have been described. See, e.g., U.S. Pat. No. 4,011,308 to Giaever, U.S. Pat. No. 4,722,890 to Sanders et al., Re. 032696 to Schuurs et al., U.S. Pat. No. 4,016,043 to Schuurs et al., U.S. Pat. No. 3,876,504 to Koffler, U.S. Pat. No. 3,770,380 to Smith, and U.S. Pat. No. 4,372,745 to Mandle et al.

Another technique for detecting biological compounds is fluorescence in situ hybridization (FISH). Swiger et al. (1996) *Environ. Mol. Mutagen.* 27:245–254; Raap (1998) *Mut. Res.* 400:287–298; Nath et al. (1997) *Biotechnic. Histol.* 73:6–22. FISH allows detection of a predetermined target oligonucleotide, e.g., DNA or RNA, within a cellular or tissue preparation by, for example, microscopic visualization. Thus, FISH is an important tool in the fields of, for example, molecular cytogenetics, pathology and immunology in both clinical and research laboratories.

This method involves the fluorescent tagging of an oligonucleotide probe to detect a specific complementary DNA or RNA sequence. Specifically, FISH involves incubating an oligonucleotide probe comprising an oligonucleotide that is complementary to at least a portion of the target oligonucleotide with a cellular or tissue preparation containing or suspected of containing the target oligonucleotide. A detectable label, e.g., a fluorescent dye molecule, is bound to the oligonucleotide probe. A fluorescence signal generated at the site of hybridization is typically visualized using an epi fluorescence microscope. An alternative approach is to use an oligonucleotide probe conjugated with an antigen such as biotin or digoxygenin and a fluorescently tagged antibody directed toward that antigen to visualize the hybridization of the probe to its DNA target. A variety of FISH formats are known in the art. See, e.g., Dewald et al. (1993) *Bone Marrow Transplantation* 12:149–154; Ward et al. (1993) *Am. J. Hum. Genet.* 52:854–865; Jalal et al. (1998) *Mayo Clin. Proc.* 73:132–137; Zahed et al. (1992) *Prenat. Diagn.* 12:483–493; Kitadai et al. (1995) *Clin. Cancer Res.* 1:1095–1102; Neuhaus et al. (1999) *Human Pathol.* 30:81–86; Hack et al., eds., (1980) *Association of Cytogenetic Technologists Cytogenetics Laboratory Manual.* (Association of Cytogenetic Technologists, San Francisco, Calif.); Buno et al. (1998) *Blood* 92:2315–2321; Patterson et al. (1993) *Science* 260:976–979; Patterson et al. (1998) *Cytometry* 31:265–274; Borzi et al. (1996) *J. Immunol. Meth.* 193:167–176; Wachtel et al. (1998) *Prenat. Diagn.* 18:455–463; Bianchi (1998) *J. Perinat. Med.* 26:175–185; and Munne (1998) *Mol. Hum. Reprod.* 4:863–870.

FISH provides a powerful tool for the chromosomal localization of genes whose sequences are partially or fully known. Other applications of FISH include in situ localization of mRNA in tissues sample and localization of nongenetic DNA sequences such as telomeres.

Signal amplification is yet another method for sensitive detection of nucleic acids and other receptor/ligand interactions. Direct detection of a target nucleic acid is possible by hybridization of a complementary nucleic acid probe to the target. Detection of the complex can be achieved by numerous means, e.g., a labeled probe or a reagent dye that specifically attaches to the target/probe complex. Such "direct" detection systems are often not sensitive enough to detect a target nucleic acid in a biological sample. One method for overcoming this limitation is to employ signal amplification. Signal amplification can be done, for example, by indirectly binding multiple signal-generating molecules to an analyte through a molecule which is (1) complementary to the analyte and (2) contains multiple signal-generating molecule binding sites and which signal-generating molecules (i) contain a detectable label, (ii) bind to or otherwise activate a label or (iii) contain sites for binding additional layers of molecules which may in turn facilitate generation of a detectable signal. Thus, rather than a single signal-generating label associated with the target molecule, signal amplification results in the association of multiple signal-generating labels associated with the target molecule and, therefore, enhanced assay sensitivity.

Nucleic acid hybridization assays are described in, for example, U.S. Pat. No. 5,681,697 to Urdea et al., U.S. Pat. No. 5,124,246 to Urdea et al., U.S. Pat. No. 4,868,105 to Urdea et al., and European Patent Publication No. 70.685, inventors Heller et al.

There are many assays designed to obtain the sequence of a DNA sample. Each of these methods shares some or all of a set of common features. These features include: sequence specificity derived from complementary oligonucleotide hybridization or annealing; a solid support or solid phase which allows separation of specifically bound assay reagents; and a label which is used for detecting the presence or absence of the specific, intended assay interaction. Examples of assays designed to detect the sequence of a DNA sample can be found in U.S. Pat. No. 5,888,731 to Yager et al., U.S. Pat. No. 5,830,711 to Barany et al., U.S. Pat. No. 5,800,994 to Martinelli et al., U.S. Pat. No. 5,792,607 to Backman et al., U.S. Pat. No. 5,716,784 to Di Cesare, U.S. Pat. No. 5,578,458 to Caskey et al., U.S. Pat. No. 5,494,810 to Barany et al., U.S. Pat. No. 4,925,785 to Wang et al., U.S. Pat. No. 4,9898,617 to Landegren et al., Chemical compounds are typically evaluated for potential therapeutic utility by assaying their ability to affect, for example, enzyme activity, ligand-receptor interactions, protein-protein interactions, or the like. Evaluating the effect of each individual candidate compound on a variety of systems can be tedious and time-consuming. Accordingly, protocols have been developed to evaluate rapidly multiple candidate compounds in a particular system and/or a candidate compound in a plurality of systems. Such protocols for evaluating candidate compounds have been referred to as high throughput screening (HTS).

In one typical protocol, HTS involves the dispersal of a candidate compound into a well of a multiwell cluster plate, for example, a 96-well or higher format plate, e.g., a 384-, 864-, or 1536-well plate. The effect of the compound is evaluated on the system in which it is being tested. The "throughput" of this technique, i.e., the combination of the number of candidate compounds that can be screened and the number of systems against which candidate compounds can be screened, is limited by a number of factors, including, but not limited to: only one assay can be performed per well; if conventional dye molecules are used to monitor the effect of the candidate compound, multiple excitation sources are required if multiple dye molecules are used; and as the well size becomes small (e.g., the 1536-well plate can accept about 5 $\mu$l of total assay volume), consistent dispensing of individual components into a well is difficult and the amount of signal generated by each assay is significantly decreased, scaling with the volume of the assay.

A number of assay formats can be used for HTS assays. For example, the inhibitory effect of the candidate compound on, e.g., enzyme activity, ligand-receptor binding, and the like, can be measured by comparing the endpoint of the assay in the presence of a known concentration of the candidate to a reference which is performed in the absence of the candidate and/or in the presence of a known inhibitor compound. Thus, for example, a candidate compound can be identified which inhibits the binding of a ligand and its receptor, or which inhibits enzyme activity, decreasing the turnover of the enzymatic process. When this process (the inhibited process) is of clinical significance, the candidates are identified to be potential drugs for a particular condition.

A 1536-well plate is merely the physical segregation of sixteen assays within a single 96 well plate format. It would be advantageous to multiplex 16 assays into a single well of the 96 well plate. This would result in greater ease of dispensing reagents into the wells and in high signal output per well. In addition, performing multiple assays in a single well allows simultaneous determination of the potential of a candidate compound to affect a plurality of target systems. Using HTS strategies, a single candidate compound can be screened for activity as, e.g., a protease inhibitor, an inflammation inhibitor, an antiasthmatic, and the like, in a single assay.

Each of the above-described assay formats utilizes detectable labels to identify the analyte of interest. Radiolabeled molecules and compounds are frequently used to detect biological compounds both in vivo and in vitro. However, due to the inherent problems associated with the use of radioactive isotopes, nonradioactive methods of detecting biological and chemical compounds are often preferable.

For example, fluorescent molecules are commonly used as tags for detecting an analyte of interest. Fluorescence is the emission of light resulting from the absorption of radiation at one wavelength (excitation) followed by nearly immediate reradiation usually at a different wavelength (emission). Organic fluorescent dyes are typically used in this context. However, there are chemical and physical limitations to the use of such dyes. One of these limitations is the variation of excitation wavelengths of different colored dyes. As a result, the simultaneous use of two or more fluorescent tags with different excitation wavelengths requires multiple excitation light sources.

Another drawback of organic dyes is the deterioration of fluorescence intensity upon prolonged and/or repeated exposure to excitation light. This fading, called photobleaching, is dependent on the intensity of the excitation light and the duration of the illumination. In addition, conversion of the dye into a nonfluorescent species is irreversible. Furthermore, the degradation products of dyes are organic compounds which may interfere with the biological processes being examined.

Additionally, spectral overlap exists from one dye to another. This is due, in part, to the relatively wide emission spectra of organic dyes and the overlap of the spectra near the tailing region. Few low molecular weight dyes have a combination of a large Stokes shift, which is defined as the separation of the absorption and emission maxima, and high fluorescence output. In addition, low molecular weight dyes may be impractical for some applications because they do not provide a bright enough fluorescent signal.

Furthermore, the differences in the chemical properties of standard organic fluorescent dyes make multiple, parallel assays impractical as different chemical reactions may be involved for each dye used in the variety of applications of fluorescent labels.

Thus, there is a continuing need in the assay art for labels with the following features: (i) high fluorescent intensity (for detection in small quantities), (ii) adequate separation between the absorption and emission frequencies, (iii) good solubility, (iv) ability to be readily linked to other molecules, (v) stability towards harsh conditions and high temperatures, (vi) a symmetric, nearly gaussian emission lineshape for easy deconvolution of multiple colors, and (vii) compatibility with automated analysis. At present, none of the conventional fluorescent labels satisfies all of these requirements.

SUMMARY OF THE INVENTION

The present invention is based on the discovery that semiconductor nanocrystals can be used as reliable and sensitive detectable labels in a variety of biological and chemical formats. Semiconductor nanocrystals (also know as quantum dot and Qdot™ nanocrystals) can be produced that have characteristic spectral emissions. These spectral emissions can be tuned to a desired energy by varying the particle size, size distribution and/or composition of the particle. A targeting compound that has affinity for one or more selected biological or chemical targets is associated with the semiconductor nanocrystal. Thus, the semiconductor nanocrystal will interact or associate with the target due to the affinity of the targeting compound for the target. The location and/or nature of the association can be determined, for example, by irradiation of the sample with an energy source, such as an excitation light source. The semiconductor nanocrystal emits a characteristic emission spectrum which can be observed and measured, for example, spectroscopically.

Conveniently, emission spectra of a population of semiconductor nanocrystals can be manipulated to have linewidths as narrow as 25–30 nm, depending on the size distribution heterogeniety of the sample population, and lineshapes that are symmetric, gaussian or nearly gaussian with an absence of a tailing region. Accordingly, the above technology allows for detection of one, or even several, different biological or chemical moieties in a single reaction. The combination of tunability, narrow linewidths, and symmetric emission spectra without a tailing region provides for high resolution of multiply sized nanocrystals, e.g., populations of monodisperse semiconductor nanocrystals having multiple distinct size distributions within a system, and simultaneous detection of a variety of biological moieties.

In addition, the range of excitation wavelengths of such nanocrystals is broad and can be higher in energy than the emission wavelengths of all available semiconductor nanocrystals. Consequently, this allows the use of a single energy source, such as light, usually in the ultraviolet or blue region of the spectrum, to effect simultaneous excitation of all populations of semiconductor nanocrystals in a system having distinct emission spectra. Semiconductor nanocrystals are also more robust than conventional organic fluorescent dyes and are more resistant to photobleaching than the organic dyes. The robustness of the nanocrystal also alleviates the problem of contamination of degradation products of the organic dyes in the system being examined. Therefore, the present invention provides uniquely valuable tags for detection of biological and chemical molecules.

Accordingly, in one embodiment, the invention is directed to a method of detecting one or more target analytes in a sample containing or suspected of containing the one or more analytes, comprising the steps of:

(a) providing the sample on a solid support;

(b) combining the sample with a semiconductor nanocrystal conjugate, wherein the combining is performed under conditions that allow formation of a complex comprising the conjugate and the analyte, when present;

(c) removing any unbound conjugate; and (d) detecting the presence of the complex, if present, by monitoring a spectral emission mediated by the semiconductor nanocrystal in the complex, wherein the emission indicates the presence of one or more target analytes in the sample.

In certain embodiments, the invention is directed to a method where there is a plurality of target analytes and the method further comprises:

(a) providing a conjugate specific for each target analyte, wherein each semiconductor nanocrystal conjugate has an emission spectrum distinct from the other semiconductor nanocrystal conjugates; and (b) detecting the presence of the target analytes by monitoring the spectral emissions of the sample, wherein the emissions indicate the presence of the target analytes in the sample.

In yet another embodiment, the invention is directed to a method of detecting one or more target analytes in a sample containing or suspected of containing the one or more analytes, comprising the steps of:

(a) providing an unlabeled specific-binding molecule on a solid support;

(b) combining the sample with the specific-binding molecule, wherein the combining is performed under conditions that allow formation of a first complex comprising the specific-binding molecule and the analyte, when present;

(c) removing any unbound sample;

(d) combining the first complex with a semiconductor nanocrystal conjugate, wherein the combining is performed under conditions that allow formation of a second complex comprising the conjugate and the analyte, when present;

(e) removing any unbound conjugate;

(f) detecting the presence of the second complex, if present, by monitoring a spectral emission mediated by the semiconductor nanocrystal in the second complex, wherein the emission indicates the presence of one or more target analytes in the sample.

In certain embodiments, the method is one where there is a plurality of target analytes and the method further comprises:

(a) providing an unlabeled specific-binding molecule on a solid support specific for each target analyte and providing a semiconductor nanocrystal conjugate specific for each target analyte, wherein each semiconductor nanocrystal conjugate has an emission spectrum distinct from the other semiconductor nanocrystal conjugates; and (b) detecting the presence of the target analytes by monitoring the spectral emissions of the sample, wherein the emissions indicate the presence of the target analytes in the sample.

In yet another embodiment, the invention is directed to a method of detecting one or more target analytes in a sample containing or suspected of containing the one or more analytes, comprising the steps of:

(a) providing the sample on a solid support;

(b) combining with the sample a specific-binding molecule, wherein (i) the specific-binding molecule comprises a first member of a binding pair, and (ii) the combining is performed under conditions that allow formation of a first complex comprising the specific-binding molecule and the analyte, when present;

(c) removing any unbound specific-binding molecule;

(d) combining the first complex with a second member of the binding pair, wherein (i) the second member of the binding pair is linked to a first semiconductor nanocrystal; and (ii) the combining is performed under conditions that allow formation of a second complex comprising the binding pair and the one or more analytes;

(e) detecting the presence of the second complex, if present, by monitoring a spectral emission mediated by the first semiconductor nanocrystal in the second complex, wherein the emission indicates the presence of one or more target analytes in the sample.

In certain embodiments, the first member of the binding pair is a first antibody and the second member of the binding pair is a second antibody reactive with the first antibody; or the first member of the binding pair is biotin and the second member of the binding pair is streptavidin; or the first member of the binding pair is digoxygenin and the second member of the binding pair is an antibody directed against digoxygenin; or the first member of the binding pair is flourescein and the second member of the binding pair is an antibody directed against flourescein.

In another embodiment, the above method is one where there is more than one analyte, and the method further comprises:

combining with the sample a second specific-binding molecule, wherein (i) the second specific-binding molecule comprises a first member of a second binding pair, and (ii) the combining is performed under conditions that allow formation of a third complex comprising the second specific-binding molecule and the analyte, when present;

removing any unbound second specific-binding molecule;

combining the third complex with a second member of the second binding pair, wherein (i) the second member of the second binding pair is linked to a second semiconductor nanocrystal that has an emission spectrum distinct from the first semiconductor nanocrystal; and (ii) the combining is performed under conditions that allow formation of a fourth complex comprising the second binding pair and an analyte; and detecting the presence of the fourth complex, if present, by monitoring a second spectral emission mediated by the second semiconductor nanocrystal in the fourth complex, wherein the second emission indicates the presence of more than one target analyte in the sample.

In still a further embodiment, the invention is directed to a method of detecting one or more target analytes in a sample containing or suspected of containing the one or more analytes. The method comprises the steps of:

(a) providing a first complex comprising at least one specific-binding molecule to which is bound a semiconductor nanocrystal conjugate, wherein the semiconductor nanocrystal has a characteristic spectral emission and wherein the conjugate specifically binds to the specific-binding molecule;

(b) combining the sample with the first complex, wherein the combining is performed under conditions that allow formation of a second complex comprising the specific-binding molecule and the analyte, when present;

(c) detecting the presence of the second complex, if present, by monitoring the characteristic spectral emission of the semiconductor nanocrystal, wherein a change in the characteristic spectral emission indicates the presence of one or more target analytes in the sample.

In certain embodiments of the method above, the plurality of first complexes are provided each comprising a different specific-binding molecule each bound to a conjugate which specifically binds each specific-binding molecule and where each specific-binding molecule binds a different analyte, and wherein each conjugate bound to a different specific-binding molecule comprises a semiconductor nanocrystal that has a characteristic spectral emission distinct from the other semiconductor nanocrystals; and wherein changes in the spectral emission of any selected semiconductor nanocrystal associated with a particular specific-binding molecule in a first complex, indicates the presence of an analyte that binds to the particular specific-binding molecule.

In certain embodiments, the specific-binding molecule is radiolabeled, and when the conjugate is bound to the specific-binding molecule the semiconductor nanocrystal emits light, as described in Example 13. Further, the method may be one wherein a plurality of first complexes are provided each comprising a different specific-binding molecule each bound to a conjugate which specifically binds each specific-binding molecule and where each specific-binding molecule binds a different analyte, and wherein each conjugate bound to a different specific-binding molecule comprises a semiconductor nanocrystal that has a characteristic spectral emission distinct from the other semiconductor nanocrystals; and wherein changes in the spectral emission of any selected semiconductor nanocrystal associated with a particular specific-binding molecule in a first complex, indicates the presence of an analyte that binds to the particular specific-binding molecule.

In the methods above, the one or more analytes may be one or more polypeptides or nucleic acid sequences, either the same or different; the nucleic acid sequences may be present on one or more chromosomal fragments; the nucleic acid sequences may be DNA or RNA; the semiconductor nanocrystal conjugate may comprise an antibody, an aptamer, or at least one polymerase chain reaction primer; the specific-binding molecule may comprise a nucleic acid molecule, e.g., an oligonucleotide, DNA, RNA, an aptamer, a protein, a receptor, an antibody, a polysaccharide or a small molecule These and other embodiments of the present invention will readily occur to those of ordinary skill in the art in view of the disclosure herein.

BRIEF DESCRIPTION OF THE DRAWINGS

FIG. 1 is a pictorial representation of a Qdot™ immunosorbent assay (QISA).

FIG. 3 shows the distribution of beads among three rows (A, B and C) of eight wells with differing concentrations of semiconductor nanocrystal conjugates, as described in Example 12.

DETAILED DESCRIPTION OF THE INVENTION

Figure 1A:
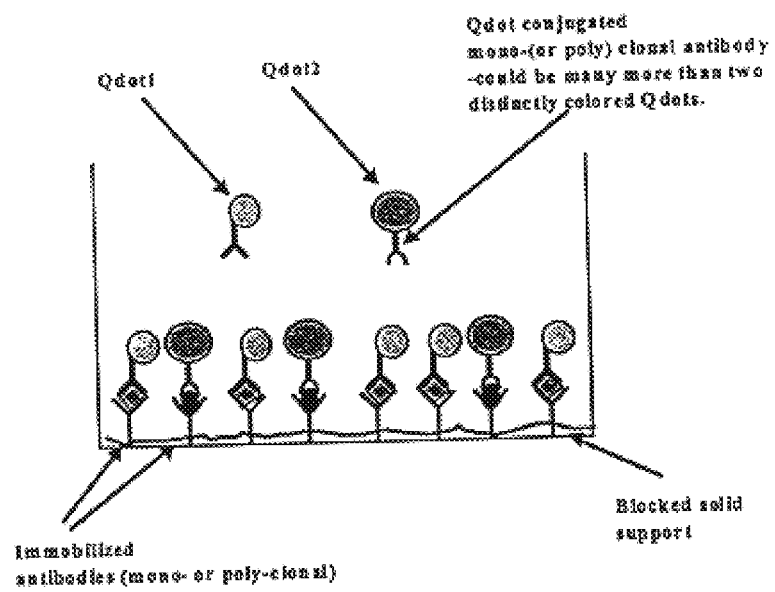
FIG. 1A is a pictorial representation of a sandwich QISA as described in Example 1.
Figure 1B:
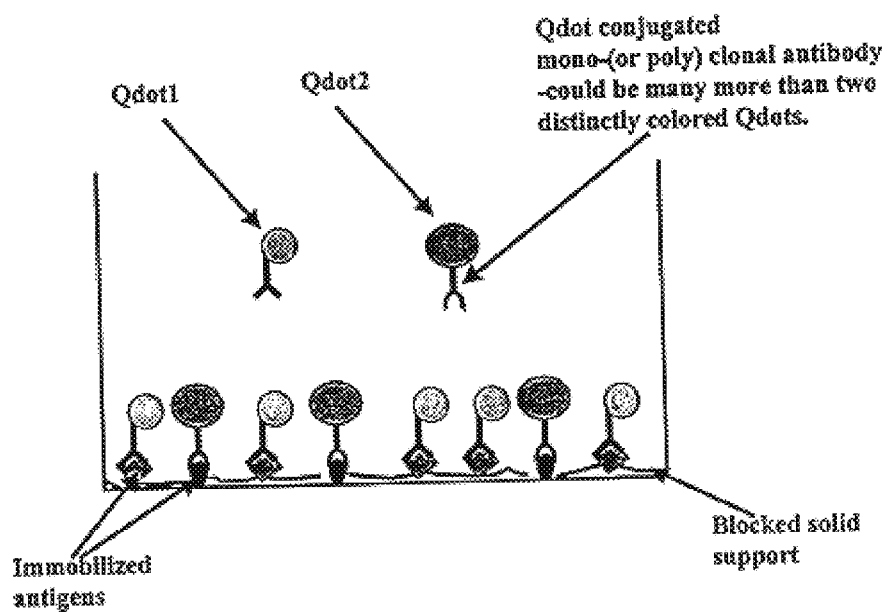
FIG. 1B is a pictorial representation of a direct capture QISA as described in Example 2.
Figure 1C:
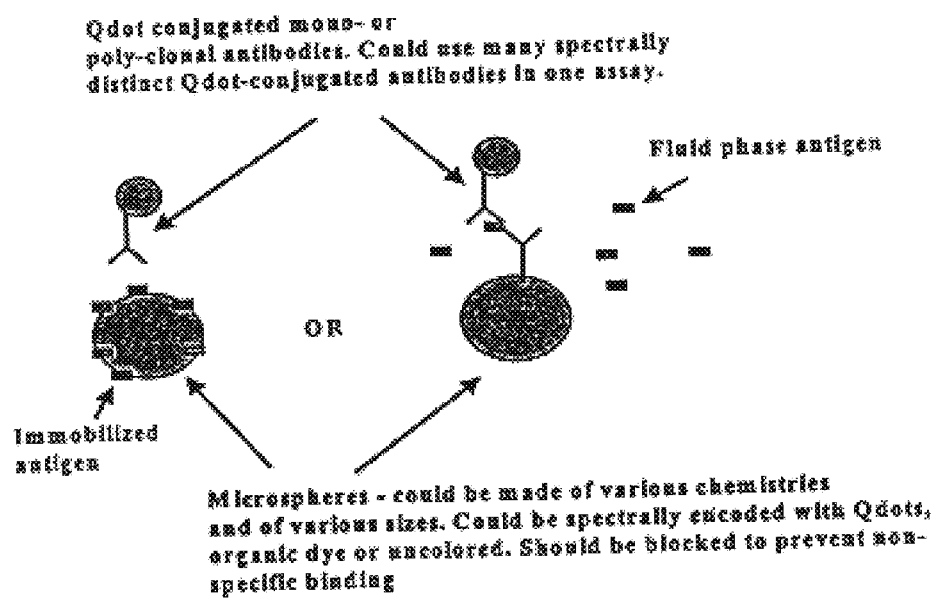
FIG. 1C is a pictorial representation of a fluid-phase QISA as described in Example 3.

The practice of the present invention will employ, unless otherwise indicated, conventional methods of chemistry and biochemistry within the skill of the art. Such techniques are explained fully in the literature.

As used in this specification and the appended claims, the singular forms "a," "an" and "the" include plural references unless the content clearly dictates otherwise. Thus, for example, reference to "a semiconductor nanocrystal" includes a mixture of two or more such semiconductor nanocrystals, an "analyte" includes more than one such analyte, and the like.

All publications, patents and patent applications cited herein, whether supra or infra, are hereby incorporated by reference in their entirety.

I. DEFINITIONS

In describing the present invention, the following terms will be employed, and are intended to be defined as indicated below.

The terms "semiconductor nanocrystal," "quantum dot" and "Qdot™ nanocrystal" are used interchangeably herein and refer to an inorganic crystallite between about 1 nm and about 1000 nm in diameter or any integer or fraction of an integer therebetween, preferably between about 2 nm and about 50 nm or any integer or fraction of an integer therebetween, more preferably about 2 nm to about 20 nm (such as about 2, 3, 4, 5, 6, 7, 8, 9, 10, 11, 12, 13, 14, 15, 16, 17, 18, 19, or 20 nm). A semiconductornanocrystal is capable of emitting electromagnetic radiation upon excitation (i.e., the semiconductor nanocrystal is luminescent) and includes a "core" of one or more first semiconductor materials, and may be surrounded by a "shell" of a second semiconductor material. A semiconductor nanocrystal core surrounded by a semiconductor shell is referred to as a "core/shell" semiconductor nanocrystal. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the group II–VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and the like) and III–V (GaN, GaP, GaAs, GaSb, InN, InP, InAs, InSb, and the like) and IV (Ge, Si, and the like) materials, and an alloy or a mixture thereof.

A semiconductor nanocrystal is, optionally, surrounded by a "coat" of an organic capping agent. The organic capping agent may be any number of materials, but has an affinity for the semiconductor nanocrystal surface. In general, the capping agent can be an isolated organic molecule, a polymer (or a monomer for a polymerization reaction), an inorganic complex, and an extended crystalline structure. The coat is used to convey solubility, e.g., the ability to disperse a coated semiconductor nanocrystal homogeneously into a chosen solvent, functionality, binding properties, or the like. In addition, the coat can be used to tailor the optical properties of the semiconductor nanocrystal. Methods for producing capped semiconductor nanocrystals are discussed further below.

Thus, the terms "semiconductor nanocrystal," "quantum dot" and "Qdot™ nanocrystal" as used herein denote a coated semiconductor nanocrystal core, as well as a core/shell semiconductor nanocrystal.

By "luminescence" is meant the process of emitting electromagnetic radiation (light) from an object. Luminescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

"Monodisperse particles" include a population of particles wherein at least about 60% of the particles in the population, more preferably 75% to 90% of the particles in the population, or any integer in between this range, fall within a specified particle size range. A population of monodispersed particles deviate less than 10% rms (root-mean-square) in diameter and preferably less than 5% rms.

The phrase "one or more sizes of semiconductor nanocrystals" is used synonymously with the phrase "one or more particle size distributions of semiconductor nanocrystals."

One of ordinary skill in the art will realize that particular sizes of semiconductor nanocrystals are actually obtained as particle size distributions.

By use of the term "a narrow wavelength band" or "narrow spectral linewidth" with regard to the electromagnetic radiation emission of the semiconductor nanocrystal is meant a wavelength band of emissions not exceeding about 40 nm, and preferably not exceeding about 20 nm in width and symmetric about the center, in contrast to the emission bandwidth of about 100 nm for a typical dye molecule with a red tail which may extend the bandwidth out as much as another 100 nm. It should be noted that the bandwidths referred to are determined from measurement of the full width of the emissions at half peak height (FWHM), and are appropriate in the range of 200 nm to 2000 nm.

By use of the term "a broad wavelength band," with regard to the excitation of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal). This onset occurs near to, but at slightly higher energy than the "narrow wavelength band" of the emission. This is in contrast to the "narrow absorption band" of dye molecules which occurs near the emission peak on the high energy side, but drops off rapidly away from that wavelength and is often negligible at wavelengths further than 100 nm from the emission.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, intemucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

The terms "polynucleotide analyte" and "nucleic acid analyte" are used interchangeably and include a single- or double-stranded nucleic acid molecule that contains a target nucleotide sequence. The analyte nucleic acids may be from a variety of sources, e.g., biological fluids or solids, chromosomes, food stuffs, environmental materials, etc., and may be prepared for the hybridization analysis by a variety of means, e.g., proteinase K/SDS, chaotropic salts, or the like.

As used herein, the term "target nucleic acid region" or "target nucleotide sequence" includes a probe-hybridizing region contained within the target molecule. The term "target nucleic acid sequence" includes a sequence with which a probe will form a stable hybrid under desired conditions.

As used herein, the term "nucleic acid probe" includes reference to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The term "aptamer" (or nucleic acid antibody) is used herein to refer to a single- or double-stranded DNA or a single-stranded RNA molecule that recognizes and binds to a desired target molecule by virtue of its shape. See, e.g., PCT Publication Nos. WO92/14843, WO91/19813, and WO92/05285, the disclosures of which are incorporated by reference herein.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

As used herein, the term "binding pair" refers to first and second molecules that specifically bind to each other. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

Exemplary binding pairs include any haptenic or antigenic compound in combination with a corresponding antibody or binding portion or fragment thereof (e.g., digoxigenin and anti-digoxigenin; fluorescein and anti-fluorescein; dinitrophenol and anti-dinitrophenol; bromodeoxyuridine and anti-bromodeoxyuridine; mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, an antibody will selectively bind to the antigen against which it was raised; A DNA molecule will bind to a substantially complementary sequence and not to unrelated sequences. The affinity molecule can comprise any molecule, or portion of any molecule, that is capable of being linked to a semiconductor nanocrystal and that, when so linked, is capable of recognizing specifically a detectable substance. Such affinity molecules include, by way of example, such classes of substances as antibodies, as defined below, monomeric or polymeric nucleic acids, aptamers, proteins, polysaccharides, sugars, and the like. See,. e.g., Haugland, "Handbook of Fluorescent Probes and Research Chemicals" (Sixth Edition), and any of the molecules capable of forming a binding pair as described above.

A "semiconductor nanocrystal conjugate" is a semiconductor nanocrystal which is linked to or associated with a specific-binding molecule, as defined above. A "semiconductor nanocrystal conjugate" includes, for example, a semiconductor nanocrystal linked or otherwise associated, through the coat, to a member of a "binding pair" or a "specific-binding molecule" that will selectively bind to a detectable substance present in a sample, e.g., a biological sample as defined herein. The first member of the binding pair linked to the semiconductor nanocrystal can comprise any molecule, or portion of any molecule, that is capable of being linked to a semiconductor nanocrystal and that, when so linked, is capable of recognizing specifically the second member of the binding pair.

The term "antibody" as used herein includes antibodies obtained from both polyclonal and monoclonal preparations, as well as, the following: hybrid (chimeric) antibody molecules (see, for example, Winter et al. (1991) *Nature* 349:293–299; and U.S. Pat. No. 4,816,567); F(ab')2 and F(ab) fragments; Fv molecules (noncovalent heterodimers, see, for example, Inbar et al. (1972) *Proc Natl Acad Sci USA* 69:2659–2662; and Ehrlich et al. (1980) *Biochem* 19:4091–4096); single-chain Fv molecules (sFv) (see, for example, Huston et al. (1988) *Proc Natl Acad Sci USA* 85:5879–5883); dimeric and trimeric antibody fragment constructs; minibodies (see, e.g., Pack et al. (1992) *Biochem*

31:1579–1584; Cumber et al. (1992) *J Immunology* 149B:120–126); humanized antibody molecules (see, for example, Riechmann et al. (1988) *Nature* 332:323–327; Verhoeyan et al. (1988) *Science* 239:1534–1536; and U.K. Patent Publication No. GB 2,276,169, published Sep. 21, 1994); and, any functional fragments obtained from such molecules, wherein such fragments retain specific-binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. Thus, the term encompasses antibodies obtained from murine hybridomas, as well as human monoclonal antibodies obtained using human rather than murine hybridomas. See, e.g., Cote, et al. *Monclonal Antibodies and Cancer Therapy*, Alan R. Liss, 1985, p. 77.

A semiconductor nanocrystal is "linked" or "conjugated" to, or "associated" with, a specific-binding molecule or member of a binding pair when the semiconductor nanocrystal is chemically coupled to, or associated with the specific-binding molecule. Thus, these terms intend that the semiconductor nanocrystal may either be directly linked to the specific-binding molecule or may be linked via a linker moiety, such as via a chemical linker described below. The terms indicate items that are physically linked by, for example, covalent chemical bonds, physical forces such van der Waals or hydrophobic interactions, encapsulation, embedding, or the like. As an example without limiting the scope of the invention, nanocrystals can be conjugated to molecules that can interact physically with biological compounds such as cells, proteins, nucleic acids, subcellular organelles and other subcellular components. For example, nanocrystals can be associated with biotin which can bind to the proteins, avidin and streptavidin. Also, nanocrystals can be associated with molecules that bind nonspecifically or sequence-specifically to nucleic acids (DNA RNA). As examples without limiting the scope of the invention, such molecules include small molecules that bind to the minor groove of DNA (for reviews, see Geierstanger and Wemmer (1995) *Ann. Rev. Biophys. Biomol. Struct.* 24:463–493; and Baguley (1982) *Mol. Cell. Biochem* 43:167–181), small molecules that form adducts with DNA and RNA (e.g. CC-1065, see Henderson and Hurley (1996) *J. Mol. Recognit.* 9:75–87; aflatoxin, see Garner (1998) *Mutat. Res.* 402:67–75; cisplatin, see Leng and Brabec (1994) *IARC Sci. Publ.* 125:339–348), molecules that intercalate between the base pairs of DNA (e.g. methidium, propidium, ethidium, porphyrins, etc., for a review see Bailly et al. *J. Mol. Recognit.* 5:155–171), radiomimetic DNA damaging agents such as bleomycin, neocarzinostatin and other enediynes (for a review, see Povirk (1996) *Mutat. Res.* 355:71–89), and metal complexes that bind and/or damage nucleic acids through oxidation (e.g. Cu-phenanthroline, see Perrin et al. (1996) *Prog. Nucleic Acid Res. Mol. Biol.* 52:123–151; Ru(II) and Os(II) complexes, see Moucheron et al. (1997) *J. Photochem. Photobiol. B* 40:91–106; chemical and photochemical probes of DNA, see Nielsen (1990) *J. Mol. Recognit.* 3:1–25.

As used herein, a "biological sample" refers to a sample of isolated cells, tissue or fluid, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

A "small molecule" is defined as including an organic or inorganic compound either synthesized in the laboratory or found in nature. Typically, a small molecule is characterized in that it contains several carbon-carbon bonds, and has a molecular weight of less than 1500 grams/Mol.

A "biomolecule" is a synthetic or naturally occurring molecule, such as a protein, amino acid, nucleic acid, nucleotide, carbohydrate, sugar, lipid and the like.

A "homogeneous assay" is one that is performed without transfer, separation or washing steps. Thus, for example, a homogeneous HTS assay involves the addition of reagents to a vessel, e.g., a test tube or sample well, followed by the detection of the results from that particular well. A homogeneous HTS assay can be performed in the solution in the test tube or well, on the surface of the test tube or well, on beads or cells which are placed into the test tube or the well, or the like. The detection system typically used is a fluorescence, chemiluminescence, or scintillation detection system.

The term "multiplexing" is used herein to include conducting an assay or other analytical method in which multiple analytes or biological states can be detected simultaneously by using more than one detectable label, each of which emits at a distinct wavelength, with a distinct intensity, with a distinct FWHM, with a distinct fluorescence lifetime, or any combination thereof. Preferably, each detectable label is linked to one of a plurality of first members of binding pairs each of which first members is capable of binding to a distinct corresponding second member of the binding pair. A multiplexed method using semiconductor nanocrystals having distinct emission spectra can be used to detect simultaneously in the range of 2 to 1,000,000, preferably in the range of 2 to 10,000, more preferably in the range of 2 to 100, or any integer between these ranges, and even more preferably in the range of up to 10 to 20, e.g., 2, 3, 4, 5, 6, 7, 8, 9, 10, 11, 12, 13, 14, 15, 16, 17, 18, 19, or 20, of analytes, biological compounds or biological states. Multiplexing also includes assays or methods in which the combination of more than one semiconductor nanocrystal having distinct emission spectra can be used to detect a single analyte.

The term "barcode" as used herein refers to one or more sizes, size distributions, compositions, or any combination thereof, of semiconductor nanocrystals. Each size, size distribution and/or composition of semiconductor nanocrystals has a characteristic emission spectrum, e.g., wavelength, intensity, FWHM, and/or fluorescent lifetime. In addition to the ability to tune the emission energy by controlling the size of the particular semiconductor nanocrystal, the intensities of that particular emission observed at a specific wavelength are also capable of being varied, thus increasing the potential information density provided by the semiconductor nanocrystal barcode system. In preferred embodiments, 2–15 different intensities may be achieved for a particular emission at a desired wavelength, however, one of ordinary skill in the art will realize that more than fifteen different intensities may be achieved, depending upon the particular application of interest. For the purposes of the present invention, different intensities may be achieved by varying the concentrations of the particular size semiconductor nanocrystal attached to, embedded within or associated with an item, compound or matter of interest. The "barcode" enables the determination of the location or identity of a particular item, compound or matter of interest. For example, semiconductor nanocrystals can be used to barcode chromosomes, as well as portions of chromosomes, for spectral karyotyping, as described further below.

"Optional" or "optionally" means that the subsequently described event or circumstance may or may not occur, and that the description includes instances where the event or circumstance occurs and instances in which it does not. For example, the phrase "optionally overcoated with a shell material" means that the overcoating referred to may or may not be present in order to fall within the scope of the invention, and that the description includes both the presence and absence of such overcoating.

II. MODES OF CARRYING OUT THE INVENTION

Before describing the present invention in detail, it is to be understood that this invention is not limited to specific assay formats, materials or reagents, as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

The present invention provides chemical and biological assays which use semiconductor nanocrystals as detectable luminescent labels to detect the presence or amount of one or more molecules, as well as to detect biological interactions, biological processes, alterations in biological processes, or alterations in the structure of a chemical or biological compound.

Semiconductor nanocrystals demonstrate quantum confinement effects in their luminescent properties. When semiconductor nanocrystals are illuminated with a primary energy source, a secondary emission of energy occurs of a frequency that corresponds to the bandgap of the semiconductor material used in the semiconductor nanocrystal. In quantum confined particles, the bandgap energy is a function of the size and/or composition of the nanocrystal. A mixed population of semiconductor nanocrystals of various sizes and/or compositions can be excited simultaneously using a single wavelength of light and the detectable luminescence can be engineered to occur at a plurality of wavelengths. The luminescent emission is related to the size and/or the composition of the constituent semiconductor nanocrystals of the population. Furthermore, semiconductor nanocrystals can be made highly luminescent through the use of a shell material which efficiently encapsulates the surface of the semiconductor nanocrystal core. A "core/shell" semiconductor nanocrystal has a high quantum efficiency and significantly improved photochemical stability. The surface of the core/shell semiconductor nanocrystal can be modified to produce semiconductor nanocrystals that can be coupled to a variety of biological molecules or substrates by techniques described in, for example, Bruchez et. al. (1998) *Science* 281:2013–2016, Chan et. al. (1998) *Science* 281:2016–2018, Bruchez "Luminescent Semiconductor Nanocrystals: Intermittent Behavior and use as Fluorescent Biological Probes" (1998) Doctoral dissertation, University of California, Berkeley, Mikulec "Semiconductor Nanocrystal Colloids: Manganese Doped Cadmium Selenide, (Core) Shell Composites for Biological Labeling, and Highly Fluorescent Cadmium Telluride" (1999) Doctoral dissertation, Massachusetts Institute of Technology, and described further below.

It is readily apparent that semiconductor nanocrystals can be used to detect or track a single target. Additionally, a population of semiconductor nanocrystals may be used for either simultaneous detection of multiple targets or to detect particular compounds and/or items of interest in, e.g., a library of compounds.

For example, compositions of semiconductor nanocrystals comprising one or more particle size distributions having characteristic spectral emissions may be used as "barcodes" in assays to either track the location or source of a particular item of interest or to identify a particular item of interest. The semiconductor nanocrystals used in such a "barcoding" scheme can be tuned to a desired wavelength to produce a characteristic spectral emission by changing the composition and size, or size distribution, of the semiconductor nanocrystal. Additionally, the intensity of the emission at a particular characteristic wavelength can also be varied, thus enabling the use of binary or higher order encoding schemes. The information encoded by the semiconductor nanocrystals can be spectroscopically decoded, thus providing the location and/or identity of the particular item or component of interest.

The ability to use semiconductor nanocrystals in order to detect multiple targets results from their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies). Upon exposure to a primary light source, each semiconductor nanocrystal distribution is capable of emitting energy in narrow spectral linewidths, as narrow as 12 nm to 60 nm FWHM, and with a symmetric, nearly Gaussian line shape, thus providing an easy way to identify a particular semiconductor nanocrystal. As one of ordinary skill in the art will realize, the linewidths are dependent on the size heterogeneity, i.e., monodispersity, of the semiconductor nanocrystals in each preparation. Single semiconductor nanocrystal complexes have been observed to have FWHM as narrow as 12 nm to 15 nm. In addition, semiconductor nanocrystal distributions with larger linewidths in the range of 35 nm to 60 nm can be readily made and have the same physical characteristics as semiconductor nanocrystals with narrower linewidths.

Semiconductor nanocrystals can be used to detect the presence and/or amount of a biological moiety, e.g., a biological target analyte; the structure, composition, and conformation of a biological molecule; the localization of a biological moiety, e.g., a biological target analyte in an environment; interactions of biological molecules; alterations in structures of biological compounds; and/or alterations in biological processes.

Thus, it is readily apparent that semiconductor nanocrystals find use in a variety of assays where other, less reliable, labeling methods have typically been used, including, without limitation, fluorescence microscopy, histology, cytology, pathology, flow cytometry, FISH and other nucleic acid hybridization assays, signal amplification assays, DNA and protein sequencing, immunoassays such as competitive binding assays and ELISAs, immunohistochemical analysis, protein and nucleic acid separation, homogeneous assays, multiplexing, high throughput screening, chromosome karyotyping, and the like.

Production of Semiconductor Nanocrystals

Semiconductor nanocrystals for use in the subject methods are made using techniques known in the art. See, e.g., U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II–VI, III–V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. The semiconductor nanocrystals are characterized by their uniform nanometer size.

As discussed above, the selection of the composition of the semiconductor nanocrystal, as well as the size of the semiconductor nanocrystal, affects the characteristic spectral emission wavelength of the semiconductor nanocrystal. Thus, as one of ordinary skill in the art will realize, a particular composition of a semiconductor nanocrystal as listed above will be selected based upon the spectral region being monitored. For example, semiconductor nanocrystals that emit energy in the visible range include, but are not limited to, CdS, CdSe, CdTe, ZnSe, ZnTe, GaP, and GaAs. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN.

For any particular composition selected for the semiconductor nanocrystals to be used in the inventive methods, it is possible to tune the emission to a desired wavelength by controlling the size of the particular composition of the semiconductor nanocrystal. In preferred embodiments, 5–20 discrete emissions (five to twenty different size populations or distributions distinguishable from one another), more preferably 10–15 discrete emissions, are obtained for any particular composition, although one of ordinary skill in the art will realize that fewer than five emissions and more than twenty emissions could be used depending on the monodispersity of the semiconductor nanocrystal particles. If high information density is required, and thus a greater number of distinct emissions, the nanocrystals are preferably substantially monodisperse within the size range given above.

As explained above, "monodisperse," as that term is used herein, means a colloidal system in which the suspended particles have substantially identical size and shape. In preferred embodiments for high information density applications, monodisperse particles deviate less than 10% rms in diameter, and preferably less than 5%. Monodisperse semiconductor nanocrystals have been described in detail in Murray et al. (1993) *J. Am. Chem. Soc.* 115:8706, and in Murray, "Synthesis and Characterization of II–VI Quantum Dots and Their Assembly into 3-D Quantum Dot Superlattices," (1995) Doctoral dissertation, Massachusetts Institute of Technology, which are hereby incorporated by reference in their entireties. One of ordinary skill in the art will also realize that the number of discrete emissions that can be distinctly observed for a given composition depends not only upon the monodispersity of the particles, but also on the deconvolution techniques employed. Semiconductor nanocrystals, unlike dye molecules, can be easily modeled as Gaussians and therefore are more easily and more accurately deconvoluted.

However, for some applications high information density will not be required and it may be more economically attractive to use more polydisperse particles. Thus, for applications that do not require high information density, the linewidth of the emission may be in the range of 40–60 nm.

In a particularly preferred embodiment, the surface of the semiconductor nanocrystal is also modified to enhance the efficiency of the emissions, by adding an overcoating layer to the semiconductor nanocrystal. The overcoating layer is particularly preferred because at the surface of the semiconductor nanocrystal, surface defects can result in traps for electrons or holes that degrade the electrical and optical properties of the semiconductor nanocrystal. An insulating layer at the surface of the semiconductor nanocrystal provides an atomically abrupt jump in the chemical potential at the interface that eliminates energy states that can serve as traps for the electrons and holes. This results in higher efficiency in the luminescent process.

Suitable materials for the overcoating layer include semiconductor materials having a higher bandgap energy than the semiconductor nanocrystal core. In addition to having a bandgap energy greater than the semiconductor nanocrystal core, suitable materials for the overcoating layer should have good conduction and valence band offset with respect to the core semiconductor nanocrystal. Thus, the conduction band is desirably higher and the valence band is desirably lower than those of the core semiconductor nanocrystal. For semiconductor nanocrystal cores that emit energy in the visible (e.g., CdS, CdSe, CdTe, ZnSe, ZnTe, GaP, GaAs) or near IR (e.g., InP, InAs, InSb, PbS, PbSe), a material that has a bandgap energy in the ultraviolet regions may be used. Exemplary materials include ZnS, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. The preparation of a coated semiconductor nanocrystal may be found in, e.g., Dabbousi et al. (1997) *J. Phys. Chem. B* 101:9463) and Kuno et al. (1997) *J. Phys. Chem.* 106:9869.

Most semiconductor nanocrystals are prepared in coordinating solvent, such as trioctylphosphine oxide (TOPO) and trioctyl phosphine (TOP) resulting in the formation of a passivating organic layer on the nanocrystal surface comprised of the organic solvent. This layer is present on semiconductor nanocrystals containing an overcoating and those that do not contain an overcoating. Thus, either of these classes of passivated semiconductor nanocrystals is readily soluble in organic solvents, such as toluene, chloroform and hexane. As one of ordinary skill in the art will realize, these functional moieties may be readily displaced or modified to provide an outer coating that renders the semiconductor nanocrystals suitable for use as the detectable labels of the present invention, as described further below. Furthermore, based upon the desired application, a portion of the semiconductor nanocrystal functionality, or the entire surface of the semiconductor nanocrystal functionality may be modified by a displacement reaction, based upon the desired use therefor.

After selection of the composition of semiconductor nanocrystal for the desired range of spectral emission and selection of a desired surface functionalization compatible with the system of interest, it may also be desirable to select the minimum number of semiconductor nanocrystals needed to observe a distinct and unique spectral emission of sufficient intensity for spectral identification. Selection criteria important in determining the minimum number of semiconductor nanocrystals needed to observe a distinct and unique spectral emission of sufficient intensity include providing a sufficient number of semiconductor nanocrystals that are bright (i.e., that emit light versus those that are dark) and providing a sufficient number of semiconductor nanocrystals to average out over the blinking effect observed in single semiconductor nanocrystal emissions. Nirmal et al., (1996) *Nature* 383:802.

For example, eight or more semiconductor nanocrystals of a particular composition and particle size distribution can be provided. If, for example, the desired method of use utilizes three different particle size distributions of a particular composition, eight of each of the three different particle size distributions of a semiconductor nanocrystal is used, in order to observe sufficiently intense spectral emissions from each to provide reliable information regarding the location or identity of a particular analyte of interest. One of ordinary skill in the art will realize, however, that fewer than eight semiconductor nanocrystals of a particular composition and particle size distribution may be utilized provided that a unique spectral emission of sufficient intensity is observed, as determined by the selection criteria set forth above.

The above method can be used to prepare separate populations of semiconductor nanocrystals, wherein each population exhibits a different characteristic photoluminescence spectrum. Each of a plurality of populations of semiconductor nanocrystals can be conjugated to distinct first members of binding pairs for use in a multiplexed assay or analytical method in which each of a plurality of corresponding second members of the binding pairs can be detected simultaneously.

The narrow spectral linewidths and nearly gaussian symmetrical lineshapes lacking a tailing region observed for the emission spectra of nanocrystals combined with the tunability of the emission wavelengths of nanocrystals allows high spectral resolution in a system with multiple nanocrystals. In theory up to 10–20 or more different-sized nanocrystals or different size distributions of monodisperse populations of nanocrystals from different preparations of nanocrystals, with each sample having a different emission spectrum, can be used simultaneously in one system, i.e., multiplexing, with the overlapping spectra easily resolved using techniques well known in the art, e.g., optically with or without the use of deconvolution software.

As discussed previously, the ability of the semiconductor nanocrystals to produce discrete optical transitions, along with the ability to vary the intensity of these optical transitions, enables the development of a versatile and dense encoding scheme. The characteristic emissions produced by one or more sizes of semiconductor nanocrystals attached to, associated with, or embedded within a particular support, compound or matter enables the identification of the analyte of interest and/or its location. For example, by providing N sizes of semiconductor nanocrystals (each having a discrete optical transition), each having M distinguishable states resulting from the absence of the semiconductor nanocrystal, or from different intensities resulting from a particular discrete optical transition, $M^n$ different states can be uniquely defined. In the case wherein M is 2, in which the two states could be the presence or absence of the semiconductor nanocrystal, the encoding scheme would thus be defined by a base 2 or binary code. In the case wherein M is 3, in which the three states could be the presence of a semiconductor nanocrystal at two distinguishable intensities and its absence, the encoding scheme would be defined by a base 3 code. Herein, such base M codes wherein M is greater than 2 are termed higher order codes. The advantage of higher order codes over a binary order code is that fewer identifiers are required to encode the same quantity of information.

As one of ordinary skill in the art will realize, the ability to develop a higher order encoding system is dependent upon the number of different intensities capable of detection by both the hardware and the software utilized in the decoding system. In particularly preferred embodiments, each discrete emission or color, is capable of being detectable at two to twenty different intensities. In a particularly preferred embodiment wherein ten different intensities are available, it is possible to employ a base 11 code comprising the absence of the semiconductor nanocrystal, or the detection of the semiconductor nanocrystal at 10 different intensities.

Clearly, the advantages of the semiconductor nanocrystals, namely the ability to observe discrete optical transitions at a plurality of intensities, provides a powerful and dense encoding scheme that can be employed in a variety of disciplines. In general, one or more semiconductor nanocrystals may act as a barcode, wherein each of the one or more semiconductor nanocrystals produces a distinct emissions spectrum. These characteristic emissions can be observed as colors, if in the visible region of the spectrum, or may also be decoded to provide information about the particular wavelength at which the discrete transition is observed. Likewise, for semiconductor nanocrystals producing emissions in the infrared or ultraviolet regions, the characteristic wavelengths that the discrete optical transitions occur at provide information about the identity of the particular semiconductor nanocrystal, and hence about the identity of or location of the analyte of interest.

The color of light produced by a particular size, size distribution and/or composition of a semiconductor nanocrystal can be readily calculated or measured by methods which will be apparent to those skilled in the art. As an example of these measurement techniques, the bandgaps for nanocrystals of CdSe of sizes ranging from 12 Å to 115 Å are given in Murray et al. (1993) *J. Am. Chem. Soc.* 115:8706. These techniques allow ready calculation of an appropriate size, size distribution and/or composition of semiconductor nanocrystals and choice of excitation light source to produce a nanocrystal capable of emitting light device of any desired wavelength.

An example of a specific system for automated detection for use with the present methods includes, but is not limited to, an imaging scheme comprising an excitation source, a monochromator (or any device capable of spectrally resolving the image, or a set of narrow band filters) and a detector array. In one embodiment, the apparatus consists of a blue or UV source of light, of a wavelength shorter than that of the luminescence detected. This may be a broadband UV light source, such as a deuterium lamp with a filter in front; the output of a white light source such as a xenon lamp or a deuterium lamp after passing through a monochromator to extract out the desired wavelengths; or any of a number of continuous wave (cw) gas lasers, including but not limited to any of the Argon Ion laser lines (457, 488, 514, etc. nm), a HeCd laser; solid state diode lasers in the blue such as GaN and GaAs (doubled) based lasers or the doubled or tripled output of YAG or YLF based lasers; or any of the pulsed lasers with output in the blue, to name a few.

The luminescence from the dots may be passed through an imaging subtracting double monochromator (or two single monochromators with the second one reversed from the first), for example, consisting of two gratings or prisms and a slit between the two gratings or prisms. The monochromators or gratings or prisms can also be replaced with a computer controlled color filter wheel where each filter is a narrow band filter centered at the wavelength of emission of one of the dots. The monochromator assembly has more flexibility because any color can be chosen as the center wavelength. Furthermore, a CCD camera or some other two dimensional detector records the images, and software color codes that image to the wavelength chosen above. The system then moves the gratings to a new color and repeats the process. As a result of this process, a set of images of the same spatial region is obtained and each is color-coded to a particular wavelength that is needed to analyze the data rapidly.

In another embodiment, the apparatus is a scanning system as opposed to the above imaging scheme. In a scanning scheme, the sample to be analyzed is scanned with respect to a microscope objective. The luminescence is put through a single monochromator or a grating or prism to spectrally resolve the colors. The detector is a diode array that then records the colors that are emitted at a particular spatial position. The software then ultimately recreates the scanned image and decodes it.

Production of Semiconductor Nanocrystal Conjugates

The present invention uses a composition comprising semiconductor nanocrystals associated with a specific-binding molecule or affinity molecule, such that the composition can detect the presence and/or amounts of biological and chemical compounds, detect interactions in biological systems, detect biological processes, detect alterations in biological processes, or detect alterations in the structure of biological compounds. Without limitation, semiconductor nanocrystal conjugates comprise any molecule or molecular complex, linked to a semiconductor nanocrystal, that can interact with a biological target, to detect biological processes, or reactions, as well as alter biological molecules or processes. Preferably, the molecules or molecular complexes or conjugates physically interact with a biological compound. Preferably, the interactions are specific. The interactions can be, but are not limited to, covalent, noncovalent, hydrophobic, hydrophilic, electrostatic, van der Waals, or magnetic. Preferably, these molecules are small molecules, proteins, or nucleic acids or combinations thereof.

Semiconductor nanocrystal conjugates can be made using techniques known in the art. For example, moieties such as TOPO and TOP, generally used in the production of semiconductor nanocrystals, as well as other moieties, may be readily displaced and replaced with other functional moieties, including, but not limited to carboxylic acids, amines, aldehydes, and styrene to name a few. One of ordinary skill in the art will realize that factors relevant to the success of a particular displacement reaction include the concentration of the replacement moiety, temperature and reactivity. Thus, for the purposes of the present invention, any functional moiety may be utilized that is capable of displacing an existing functional moiety to provide a semiconductor nanocrystal with a modified functionality for a specific use.

The ability to utilize a general displacement reaction to modify selectively the surface functionality of the semiconductor nanocrystals enables functionalization for specific uses. For example, because detection of biological compounds is most preferably carried out in aqueous media, a preferred embodiment of the present invention utilizes semiconductor nanocrystals that are solubilized in water. In the case of water-soluble semiconductor nanocrystals, the outer layer includes a compound having at least one linking moiety that attaches to the surface of the particle and that terminates in at least one hydrophilic moiety. The linking and hydrophilic moieties are spanned by a hydrophobic region sufficient to prevent charge transfer across the region. The hydrophobic region also provides a "pseudo-hydrophobic" environment for the nanocrystal and thereby shields it from aqueous surroundings. The hydrophilic moiety may be a polar or charged (positive or negative) group. The polarity or charge of the group provides the necessary hydrophilic interactions with water to provide stable solutions or suspensions of the semiconductor nanocrystal. Exemplary hydrophilic groups include polar groups such as hydroxides (—OH), amines, polyethers, such as polyethylene glycol and the like, as well as charged groups, such as carboxylates (—$CO^{2-}$), sulfonates (—$SO^{3-}$), phosphates (—$PO_4^{2-}$ and —$PO_3^{2-}$), nitrates, ammonium salts (—$NH^{4+}$), and the like. A water-solubilizing layer is found at the outer surface of the overcoating layer. Methods for rendering semiconductor nanocrystals water-soluble are known in the art and described in, e.g., International Publication No. WO 00/17655, published Mar. 30, 2000.

The affinity for the nanocrystal surface promotes coordination of the linking moiety to the semiconductor nanocrystal outer surface and the moiety with affinity for the aqueous medium stabilizes the semiconductor nanocrystal suspension.

A displacement reaction may be employed to modify the semiconductor nanocrystal to improve the solubility in a particular organic solvent. For example, if it is desired to associate the semiconductor nanocrystals with a particular solvent or liquid, such as pyridine, the surface can be specifically modified with pyridine or pyridine-like moieties to ensure solvation.

The surface layer may also be modified by displacement to render the semiconductor nanocrystal reactive for a particular coupling reaction. For example, displacement of TOPO moieties with a group containing a carboxylic acid moiety enables the reaction of the modified semiconductor nanocrystals with amine containing moieties (commonly found on solid support units) to provide an amide linkage. Additional modifications can also be made such that the semiconductor nanocrystal can be associated with almost any solid support. A solid support, for the purposes of this invention, is defined as an insoluble material to which compounds are attached during a synthesis sequence, screening, immunoassays, etc. The use of a solid support is particularly advantageous for the synthesis of libraries because the isolation of support-bound reaction products can be accomplished simply by washing away reagents from the support-bound material and therefore the reaction can be driven to completion by the use of excess reagents.

A solid support can be any material that is an insoluble matrix and can have a rigid or semi-rigid surface. Exemplary solid supports include but are not limited to pellets, disks, capillaries, hollow fibers, needles, pins, solid fibers, cellulose beads, poreglass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

For example, the semiconductor nanocrystals of the present invention can readily be functionalized to create styrene or acrylate moieties, thus enabling the incorporation of the semiconductor nanocrystals into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

For a detailed description of these linking reactions, see, e.g., U.S. Pat. No. 5,990,479; Bruchez et. al. (1998) *Science* 281:2013–2016., Chan et. al. (1998) *Science* 281:2016–2018, Bruchez "Luminescent Semiconductor Nanocrystals: Intermittent Behavior and use as Fluorescent Biological Probes" (1998) Doctoral dissertation, University of California, Berkeley, and Mikulec "Semiconductor Nanocrystal Colloids: Manganese Doped Cadmium Selenide, (Core)Shell Composites for Biological Labeling, and Highly Fluorescent Cadmium Telluride" (1999) Doctoral dissertation, Massachusetts Institute of Technology.

Semiconductor Nanocrystals as Detection Reagents in Immunoassays

In one embodiment of the invention, immunoassays, such as immunosorbent assays, are provided in which semiconductor nanocrystal conjugates are used as the detection reagents. A Qdot™ immunosorbent assay (QISA) has several advantages over current immunosorbent assays including, but not limited to, simultaneous multicolor detection and, hence, multiple analyte detection, no requirement for enzyme development, increased photostability over alternative fluorophores thereby allowing increased detection sensitivity by virtue of the ability to monitor the signal over a long period of time, increased sensitivity over enzyme-based detection systems.

Semiconductor nanocrystals of varying core sizes (10–150 Å), composition and/or size distribution are conjugated to specific-binding molecules which bind specifically to an analyte of interest. Any specific anti-analyte can be used, for example, an antibody, an immunoreactive fragment of an antibody, and the like. Preferably, the anti-analyte is an antibody. The semiconductor nanocrystal conjugates are used in an immunosorbent assay to detect any analyte for which a specific-binding agent exists.

More specifically, the specific-binding molecule may be derived from polyclonal or monoclonal antibody preparations, may be a human antibody, or may be a hybrid or chimeric antibody, such as a humanized antibody, an altered antibody, F(ab')$_2$ fragments, F(ab) fragments, Fv fragments, a single-domain antibody, a dimeric or trimeric antibody fragment construct, a minibody, or functional fragments thereof which bind to the analyte of interest. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, polyclonal antibodies are generated by immunizing a suitable animal, such as a mouse, rat, rabbit, sheep or goat, with an antigen of interest. In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2–6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler and Milstein (1975) *Nature* 256:495–497, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

Human monoclonal antibodies are obtained by using human rather than murine hybridomas. See, e.g., Cote, et al. *Monclonal Antibodies and Cancer Therapy*, Alan R. Liss, 1985, p. 77.

Monoclonal antibodies or portions thereof may be identified by first screening a B-cell cDNA library for DNA molecules that encode antibodies that specifically bind to p185, according to the method generally set forth by Huse et al. (1989) *Science* 246:1275–1281. The DNA molecule may then be cloned and amplified to obtain sequences that encode the antibody (or binding domain) of the desired specificity.

As explained above, antibody fragments which retain the ability to recognize the analyte of interest, will also find use in the subject immunoassays. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments will contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as F$_V$. See, e.g., Inbar et al. (1972) *Proc. Nat. Acad. Sci. USA* 69:2659–2662; Hochman et al. (1976) *Biochem* 15:2706–2710; and Ehrlich et al. (1980) *Biochem* 19:4091–4096.

A single-chain Fv ("sFv" or "scFv") polypeptide is a covalently linked $V_H$–$V_L$ heterodimer which is expressed from a gene fusion including $V_H$- and $V_L$-encoding genes linked by a peptide-encoding linker. Huston et al. (1988) *Proc. Nat. Acad. Sci. USA* 85:5879–5883. A number of methods have been described to discern and develop chemical structures (linkers) for converting the naturally aggregated, but chemically separated, light and heavy polypeptide chains from an antibody V region into an sFv molecule which will fold into a three dimensional structure substantially similar to the structure of an antigen-binding site. See, e.g., U.S. Pat. Nos. 5,091,513, 5,132,405 and 4,946,778. The sFv molecules may be produced using methods described in the art. See, e.g., Huston et al. (1988) *Proc. Nat. Acad. Sci. USA* 85:5879–5883; U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" will also find use with the present invention. Minibodies are sFv polypeptide chains which include oligomerization domains at their C-termini, separated from the sFv by a hinge region. Pack et al. (1992) *Biochem* 31:1579–1584. The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) *Biochem* 31:1579–1584; Cumber et al. (1992) *J Immunology* 149B:120–126.

Once produced, the specific-binding molecules described above may be used in immunoassays of varying formats. For example, the antibodies may be linked to the semiconductor nanocrystal. Alternatively, the semiconductor nanocrystals may be linked to other affinity molecules, such as strepavidin, that will specifically react with another molecule that is linked to the analyte of interest.

The analyte of interest can be detected using standard immunoassays such as competition, direct reaction, or sandwich type assays. Such assays include, but are not limited to, ELISA-like assays (termed QISA herein) and biotin/avidin type assays. The reactions include the semiconductor nanocrystals in order to detect the formation of a complex between the antigen and the antibody or antibodies reacted therewith.

The aforementioned assays generally involve separation of unbound antibody in a liquid phase from a solid phase support to which labeled antigen-antibody complexes are bound. Solid supports which can be used in the methods herein include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In one context, a solid support is first reacted with a component that will bind to the solid support, i.e., the "solid phase component," e.g., an antigen or an antibody, under suitable binding conditions such that the component is sufficiently immobilized to the support. Sometimes, immobilization to the support can be enhanced by first coupling the antigen or antibody to a protein with better solid phase-binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other reagents that can be used to bind molecules to the support include polysaccharides, polylactic acids, polyglycolic acids, polymeric amino acids, amino acid copolymers, and the like. Such molecules and methods of coupling these molecules to antigens, are well known to those of ordinary skill in the art. See, e.g., Brinkley, M. A. (1992) *Bioconjugate Chem*. 3:2–13; Hashida et al. (1984) *J. Appl. Biochem*. 6:56–63; and Anjaneyulu and Staros (1987) *International J. of Peptide and Protein Res*. 30:117–124.

After reacting the solid support with the solid phase component, any nonimmobilized solid-phase components are removed from the support by washing, and the support-bound component is then contacted with a biological sample suspected of containing ligand moieties (e.g., antibodies toward the immobilized antigens, or antigens toward immobilized antibodies) under suitable binding conditions. After washing to remove any nonbound ligand, a secondary binder moiety detectably labeled with the semiconductor nanocrystals described herein is added under suitable binding conditions, wherein the secondary binder is capable of associating selectively with the bound ligand. The presence of the secondary binder can then be detected using the techniques described above. Alternatively, an indirect labeling technique can be used wherein the presence of an unlabeled secondary binder moiety is detected by the specific binding thereto of a detectably labeled tertiary binder moiety.

More particularly, a QISA method can be used, wherein the wells of a microtiter plate are coated with a selected antigen. A biological sample containing or suspected of containing antibodies to the antigen is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected as described above.

Thus, in one particular embodiment, the presence of bound antibody ligands from a biological sample can be readily detected using a secondary binder comprising an antibody directed against the antibody ligands, conjugated to semiconductor nanocrystals. A number of immunoglobulin (Ig) molecules are known in the art which can be readily conjugated to semiconductor nanocrystals as described herein. In other related embodiments, competitive-type QISA techniques can be practiced using methods known to those skilled in the art.

Assays can also be conducted in solution, such that the antigens and antibodies specific for those proteins form complexes under precipitating conditions. In one particular embodiment, antigens can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the antigen. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing a particular antigen is immobilized to a substrate. In this regard, an initial affinity purification of the sample can be carried out using immobilized antigens. The resultant sample preparation will thus only contain specific antibodies, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, semiconductor nanocrystal-labeled proteins are contacted with the bound antibodies under suitable binding conditions. After any nonspecifically bound antigen has been washed from the immunoaffinity support, the presence of bound antigen can be determined by assaying for label using methods described above.

Additionally, antibodies raised to particular antigens, rather than the antigens themselves, can be used in the above-described assays in order to detect the presence of a protein of interest in a given sample. These assays are performed essentially as described above and are well known to those of skill in the art.

In yet further embodiments, semiconductor nanocrystal-antibody conjugates may be used to probe fixed tissue samples or fixed cell populations for specific markers. In this embodiment, prepared cells or tissue are incubated with an antibody which is conjugated to a semiconductor nanocrystal. Semiconductor nanocrystals allow stable, multicolor detection of markers in both cell and tissue samples.

Semiconductor nanocrystal-conjugates (either a single semiconductor nanocrystal conjugated to biomolecules or a plurality of semiconductor nanocrystals) allow specific, sensitive, photostable detection of antigens in staining procedures. This offers a clear advantages over currently available stains. Additionally the inherent properties of semiconductor nanocrystals, i.e., single excitation source, narrow, gaussian spectra and tunability of emission wavelength, mean that many more colors are resolved than with conventional fluorescent dyes.

More particularly, multiple analysis staining can be performed on a tissue sample, blood sample or any sample requiring multiplexed analysis of cellular or extracellular markers. The procedure may be carried out in a two-step reaction whereby a primary antibody is followed by a semiconductor nanocrystal-conjugated antibody or by using an antibody (or other biomolecule) semiconductor nanocrystal conjugate to directly label the sample. For example, five (or more with increased spectral use or reduced spectral separation) different populations of semiconductor nanocrystals can be synthesized with emission spectra that are spaced at 40 nm intervals from, e.g., 490–650 nm. Each spectrally distinct population of semiconductor nanocrystals is conjugated to a different molecule which specifically recognizes a biomolecule of interest which may or may not be present in the sample to be analyzed. Following standard staining protocols, the sample is labeled with the semiconductor nanocrystals and analyzed for the location and quantity of the target molecule. This analysis may be carried out by conventional fluorescent microscopy techniques or by use of a spectral scanning device as described above.

Since many semiconductor nanocrystals can be generated that are spectrally distinct, it is possible to label different items such as antibodies or cDNAs that can then be used to measure the position and quantity of cellular compounds (as described above). The number of compounds that can be followed is limited, however, by the number of spectrally distinct colors that can be made. With CdSe, semiconductor nanocrystals and the current synthetic techniques, this is approximately 6–7 spectrally distinct colors. If different compounds are not colocalized in the cell, however, many more semiconductor nanocrystal colors can be used by taking advantage of the known spatial separation of the targets to be analyzed. For example, no overlap would occur between nuclear localized targets and membrane localized targets. Hence organelle-specific groups of semiconductor nanocrystals can be employed to increase dramatically the number of discernable targets (see Example 18 below).

The semiconductor nanocrystals may also be used in competitive microsphere filter assays, such as competitive latex immunoassays. Such assays are described in, e.g., Stave J. W. (1994) Immunoassay for priority pollutants. *Analytica* 94 *Conference Abstracts* p. 339; and Bangs, L. B. (1996) Immunological Applications of Microspheres. In *The Latex Course* 4196. Traditionally, this assay uses antibody-conjugated latex particles to detect industrial chemicals in soil or ground water samples at parts per billion concentrations. In this application the antibody is conjugated to, e.g., 3 $\mu$m microspheres which are caught on 1 $\mu$m pore filters. A sample is passed through the filter and the immobilized antibodies catch any antigen present. An enzyme/antigen conjugate is passed through the filter. If the sample contains no antigen then the enzyme/antigen will bind to the free sites on the antibody and added substrate will cause a color change on the filter. Increases in antigen concentration will result in corresponding decreases in the filter color change.

In the context of the present invention, the detection agent is a semiconductor nanocrystal or a semiconductor nanocrystal-encoded solid conjugate. The conjugate is a molecule that specifically recognizes the analyte. The antigen conjugates are direct semiconductor nanocrystal-antigen conjugates or semiconductor nanocrystal-dyed microsphere-conjugates that are small enough to pass through filter pores. This allows multiple simultaneous detections using a light source for excitation of the semiconductor nanocrystals and detection of emissions. The detection takes place on the filter or in the filtrate and the assay may be carried out in a high throughput multiwell environment. The filters in this format are opaque to the excitation light and allow detection of semiconductor nanocrystals in the filtrate without the need for washes or sample removal. Analyte concentration, in virtually any context where a specific binder exists for that analyte, can be determined. Thus, almost any analyte, chemical or biological, organic or inorganic may be detected in this manner.

The detection is achieved by competition between analyte in the sample and analyte conjugated to semiconductor nanocrystals or conjugated to a semiconductor nanocrystal-encoded microsphere which is small enough to pass through the filter pores. Separation is achieved because the reaction is free to pass through a microporous filter in which the pores are a smaller size than the diameter of the microsphere. Thus the microsphere cannot pass through the filter (see FIG. 5). Semiconductor nanocrystal-conjugates or semiconductor nanocrystal encoded microspheres are of small enough size to pass through the filter and will do so unless bound to the microspheres. If a known amount of semiconductor nanocrystals are applied to the upper level, with the analyte sample, allowed to bind for a predetermined time and then passed through the filter, the concentration of the analyte is determined by measuring the level of fluorescence present in the lower level. Fluorescence in the upper level is not detected either by removal of the upper level or because the membrane is opaque to the excitation source.

Detection is carried out by a spectral sensing device and separation of different semiconductor nanocrystal spectra is achieved by the use of band-pass filters or by measuring light emission across the spectrum. Detection can be achieved by a static detection device or by a scanning detector, as described above.

Semiconductor Nanocrystals as Detection Reagents in Probe-based Assays

Semiconductor nanocrystals can also be used as sensitive detection agents in probe-based assays for the detection of target nucleic acid sequences in test samples. Probes for use in these assays are designed from either conserved or nonconserved regions of the target polynucleotide of interest, using techniques well known in the art. Generally, probes are developed from nonconserved or unique regions when maximum specificity is desired, and from conserved regions when assaying for regions that are closely related to, for example, different members of a multigene family or in related species.

Polymerase chain reaction (PCR) is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. PCR is described in U.S. Pat. Nos. 4,683,195 and 4,683,202, which are incorporated herein by reference in their entireties.

The Ligase Chain Reaction (LCR) is an alternate method for nucleic acid amplification. In LCR, probe pairs are used which include two primary (first and second) and two secondary (third and fourth) probes, all of which are used in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship. Thus, a ligase can covalently fuse or ligate the two probes into a fused product. In addition, a third (secondary) probe can hybridize to a portion of the first probe and a fourth (secondary) probe can hybridize to a portion of the second probe in a similar abutting fashion. If the target is initially double-stranded, the secondary probes will also hybridize to the target complement in the first instance. Once the ligated strand of primary probes is separated from the target strand, it will hybridize with the third and fourth probes which can be ligated to form a complementary, secondary ligated product. By repeated cycles of hybridization and ligation, amplification of the target sequence is achieved. This technique is described in, e.g., European Publication No. 320,308, published Jun. 16, 1989 and European Publication No. 439,182, published Jul. 31, 1991.

More particularly, in the above methods, once the primers or probes have been sufficiently extended and/or ligated, they are separated from the target sequence, for example, by heating the reaction mixture to a "melt temperature" which dissociates the complementary nucleic acid strands. Thus, a sequence complementary to the target sequence is formed. A new amplification cycle can then take place to further amplify the number of target sequences by separating any double-stranded sequences, allowing primers or probes to hybridize to their respective targets, extending and/or ligating the hybridized primers or probes and reseparating. The complementary sequences that are generated by amplification cycles can serve as templates for primer extension or fill the gap of two probes to firther amplify the number of target sequences. Typically, a reaction mixture is cycled between 20 and 100 times, more typically between 25 and 50 times. In this manner, multiple copies of the target sequence and its complementary sequence are produced. Thus, primers initiate amplification of the target sequence when it is present under amplification conditions.

mRNAs may be amplified by reverse transcribing the mRNA into cDNA, and then performing PCR (RT-PCR), as described above. Alternatively, a single enzyme may be used for both steps as described in U.S. Pat. No. 5,322,770, which is incorporated herein by reference. mRNA may also be reverse transcribed into cDNA, followed by asymmetric gap ligase chain reaction (RT-AGLCR) as described by Marshall et al. (1994) *PCR Meth. App.* 4:80–84.

Other known amplification methods which can be utilized in probe-based assays include, but are not limited to, the "NASBA" or "3SR" (Guatelli et al. (1990) *Proc. Natl. Acad. Sci. USA* 87:1874–1878 and Compton, J. *Nature* 350:91–92); Q-beta amplification; strand displacement amplification (Walker et al. *Clin. Chem.* 42:9–13 and European Patent Application No. 684,315); and target mediated amplification (International Publication No. WO 93/22461).

Detection, both amplified and nonamplified, may be performed using a variety of heterogeneous and homogeneous detection formats. Examples of heterogeneous detection formats are disclosed in Snitman et al., U.S. Pat. No. 5,273,882; Urdea et al., U.S. Pat. No. 5,124,246; Ullman et al. U.S. Pat. No. 5,185,243; and Kourilsky et al., U.S. Pat. No. 4,581,333, all of which are incorporated herein by reference in their entireties. Examples of homogeneous detection formats are described in Caskey et al., U.S. Pat. No. 5,582,989; and Gelfand et al., U.S. Pat. No. 5,210,015, which are incorporated herein by reference in their entireties. Also contemplated and within the scope of the present invention is the use of multiple probes in hybridization assays, to improve sensitivity and amplification of the target signal. See, for example, Caskey et al., U.S. Pat. No. 5,582,989; and Gelfand et al., U.S. Pat. No. 5,210,015; which are incorporated herein by reference in their entireties.

Thus, in one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method provided herein are labeled with capture and detection labels, wherein probes are labeled with one type of label and primers are labeled with another type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double-stranded because primers are provided to amplify a target sequence and its complementary strand. The double-stranded amplicon then is thermally denatured to produce single-stranded amplicon members. Upon formation of the single-stranded amplicon members, the mixture is cooled to allow the formation of complexes between the probes and single-stranded amplicon members.

As the single-stranded amplicon sequences and probe sequences are cooled, the probe sequences preferentially bind the single-stranded amplicon members. After the probe/single-stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. Either the capture label or detection label comprises semiconductor nanocrystals. In cases where the detection label is directly detectable, the presence of the hybrids on the solid phase can be detected using techniques described above. In cases where the label is not directly detectable, the captured hybrids can be contacted with a conjugate, which generally comprises a binding member attached to a semiconductor nanocrystal label. The conjugate becomes bound to the complexes and the presence of the conjugate on the complexes can be detected with the directly detectable semiconductor nanocrystal label. Thus, the presence of the hybrids on the solid-phase reagent can be determined. Wash steps are typically employed during the above reactions to wash away unhybridized amplicon or probe as well as unbound conjugate.

The heterogeneous assays can be conveniently performed using a solid phase support that carries an array of nucleic acid molecules. Such arrays are useful for high-throughput and/or multiplexed assay formats, described in more detail below. Various methods for forming such arrays from preformed nucleic acid molecules, or methods for generating the array using in situ synthesis techniques, are generally known in the art. (See, for example, Dattagupta, et al., European Publication No. 234,726; U.S. Pat. No. 5,700,637 to Souther; U.S. Pat. No. 5,143,854 to Pirrung, et al.; International Publication No. WO 92/10092; and, Fodor, et al. (1991) Science 251:767–777.

Although the target sequence above is described as single-stranded, the target may also be double-stranded and separated from its complement prior to hybridization with the amplification primer sequences. Further, while the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Publication No. WO 92/20702; morpholino analogs which are described in U.S. Pat. Nos. 5,185,444, 5,034,506 and 5,142,047; and the like. Depending upon the type of label carried by the probe, the probe is employed to capture or detect the amplicon generated by the amplification reaction.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

As explained above, aptamers are single- or double-stranded DNA or single-stranded RNA molecules that recognize and bind to a desired target molecule by virtue of their shapes. See, e.g., PCT Publication Nos. WO92/14843, WO91/19813, and WO92/05285. The SELEX procedure, described in U.S. Pat. No. 5,270,163 to Gold et al., Tuerk et al. (1990) Science 249:505–510, Szostak et al. (1990) Nature 346:818–822 and Joyce (1989) Gene 82:83–87, can be used to select for RNA or DNA aptamers that are target-specific. In the SELEX procedure, an oligonucleotide is constructed wherein an n-mer, preferably a randomized sequence of nucleotides thereby forming a "randomer pool" of oligonucleotides, is flanked by two polymerase chain reaction (PCR) primers. The construct is then contacted with a target molecule under conditions which favor binding of the oligonucleotides to the target molecule. Those oligonucleotides which bind the target molecule are: (a) separated from those oligonucleotides which do not bind the target molecule using conventional methods such as filtration, centrifugation, chromatography, or the like; (b) dissociated from the target molecule; and (c) amplified using conventional PCR technology to form a ligandenriched pool of oligonucleotides. Further rounds of binding, separation, dissociation and amplification are performed until an aptamer with the desired binding affinity, specificity or both is achieved. The final aptamer sequence identified can then be prepared chemically or by in vitro transcription. Semiconductor nanocrystals are readily used in the detection of such aptamers.

Specific embodiments of the above-described probe-based assays are described in further detail below.

Semiconductor Nanocrystals for Detection Reagents in Fluorescence in situ Hybridization In another embodiment of the invention, FISH assays using a semiconductor nanocrystal as a detectable label are disclosed. Techniques for performing various types of FISH assays are well known in the art and described in, e.g., Raap, A. K. (1998) Mutation Res. 400:287–298; Speel et al. (1998) Histochem. Cell. Biol. 110:571–577; Nath and Johnson (1997) Biotech. Histochem. 73:6–22; Swiger and Tucker (1996) Environ. Molec. Mutagen. 27:245–254; Kitadai et al. (1995) Clin. Cancer Res. 1:1095–1102; Heiskanen et al. (1995) Genomics 30:31–36; and Heiskanen et al. (1994) BioTechniques 17:928–933. Semiconductor nanocrystals can be substituted for the fluorescent labels normally used in each of these techniques. The advantages of nucleic acid probes labeled with semiconductor nanocrystals is that multiple probes directed at distinct target oligonucleotides can be used simultaneously by virtue of the fact that a plurality of populations of semiconductor nanocrystals can be made with nonoverlapping emission spectra, each of which can be excited with a single source and wavelength of light. The ability to "multiplex" assays in this manner is especially useful when the specimen to be analyzed contains a limited source of cells or tissues, e.g., rare cells, fetal cells in maternal blood, cancer cells in blood or urine samples, blastomeres, or the like. By multiplexing, multiparametric information at the single cell level may be collected. See, e.g., Patterson et al. (1998) Cytometry 31:265–274; Borzi et al. (1996) J. Immunol. Meth. 193:167–176; Wachtel et al. (1998) Prenat. Diagn. 18:455–463; Bianchi (1998) J. Perinat. Med. 26:175–185; and Munne (1998) Mol. Hum. Reprod. 4:863–870.

Semiconductor nanocrystals of many colors can be chemically linked to nucleic acid (DNA or RNA) or indirectly linked to streptavidin/biotin that binds to nucleic acid. Semiconductor nanocrystals bind to DNA primers or incorporate into nucleic acid by using semiconductor nanocrystal-linked nucleotide(s). PCR can be used to generate nucleic acid fragments for FISH probes. Semiconductor nanocrystals can also be chemically attached to a nucleic acid containing the sequence of interest. Alternatively, biotin molecules can be attached to oligonucleotide primers, or incorporated into nucleic acid of interest by using biotinlyated nucleotides in PCR. Semiconductor nanocrystals attached to streptavidin will then be linked to biotin in the nucleic acid probe. These semiconductor nanocrystal-FISH probes can be use for in situ hybridization for DNA (see Example 5; see also Dewald et al. (1993) *Bone Marrow Transplantation* 12:149–154; Ward et al. (1993) *Am. J. Hum. Genet.* 52:854–865; Jalal et al. (1998) *Mayo Clin. Proc.* 73:132–137; Zahed et al. (1992) *Prenat. Diagn.* 12:483–493; Neuhaus et al. (1999) *Human Pathol.* 30:81–86; Buno et al. (1998) *Blood* 92:2315–2321; Munne (1998) *Mol. Hum. Reprod.* 4:863–870, and RNA (see Example 6; Kitadai et al. (1995) *Clin. Cancer Res.* 1:1095–1102). The results can be analyzed, for example, under an epi fluorescence microscope. Semiconductor nanocrystal-FISH probe or probes for DNA and RNA together (see Example 7; Wachtel et al. (1998) *Prenat. Diagn.* 18:455–463), or for RNA and surface immunophenotyping together (see Example 8; Patterson et al. (1998) *Cytometry* 31:265–274; Borzi et al. (1996) *J. Immunol. Meth.* 193:167–176) can be used to identify, sort, and analyze rare cells simultaneously. In the case where only short oligonucleotide semiconductor nanocrystals-FISH probes (forward and reverse primers) for RNA or DNA are available, sensitivity of probes can be increased through PCR/FISH or RT-PCR/FISH. This can be accomplished by incorporating a semiconductor nanocrystal-dNTP into the in situ PCR or RT-PCR reaction. (see Example 9; Patterson et al. (1993) *Science* 260:976–979; Patterson et al. (1998) *Cytometry* 31:265–274). The detection system may be a microscope, or flow cytometer, or detector capable of measuring the wavelength of light emitted from the different semiconductor nanocrystals.

FISH technologies are widely used in research and clinical molecular cytogenetics, pathology and immunology laboratories. Semiconductor nanocrystal-DNA probes can be use to detect amplification (e.g., HER2/neu, c myc genes amplification), addition (e.g., trisomy 21, 13, 18), deletion (e.g., 45x, Turner's Syndrome), translocation (e.g., BCR/ABL in CML) of DNA in the nuclei.

Semiconductor nanocrystal-RNA probes can be used to localize and to monitor expression of genes (mRNA) in the cell. This is especially useful for detecting rare cells (e.g. fetal cells in maternal blood, cancer cells for monitoring disease recurrence).

In the case where only forward and reverse primers (with or without semiconductor nanocrystals attached) are available, PCR/FISH or RT-PCR/FISH can be used to amplify the target DNA or RNA to increase sensitivity. This can be accomplished by incorporating a semiconductor nanocrystal-dNTP into the in situ PCR or RT-PCR reaction.

Semiconductor nanocrystals can be conjugated to antibodies, to a protein of interest (antigen) to detect protein expression and/or sort out cells of interest. Multiple semiconductor nanocrystals-antibody(ies), semiconductor nanocrystals-nucleic acid probes for RNA and or DNA can be used to hybridize with cells in the same or sequential reaction. Cells of interest in the population (rare cells) can then be identified and analyzed for DNA (for genetic composition) or mRNA (for gene expression) simultaneously.

Specimens for FISH Assays:

Specimens can be cells (alive or fixed) or nuclei in suspension or attached to microscope slides or other solid supports or paraffin embedded tissue sections containing one, or more than one specimen, or frozen tissue sections or fine needle aspirate. FISH can be performed on metaphase or interphase cells or directly onto DNA strands.

The specimen for the FISH assay is prepared using well known methods depending on the specimen type, for example: peripheral blood (Hack et al., eds., (1980), supra; Buno et al. (1998), supra; Patterson et al. (1993), supra; Patterson et al. (1998), supra; Borzi et al. (1996), supra); bone marrow (Dewald et al. (1993), supra; Hack et al., eds., (1980), supra); amniocytes (Ward et al. (1993), supra; Jalal et al. (1998), supra); CVS (Zahed et al. (1992), supra); paraffin embedded tissue sections (Kitadai et al. (1995); supra; Neuhaus et al. (1999), supra); fetal cells (Wachtel et al. (1998), supra; Bianchi (1998), supra); and blastomeres (Munne (1998), supra).

Optimization of Conditions for FISH Assays:

The conditions of the FISH assays exemplified below can be optimized depending on the nature of different probes (e.g., whether the nucleic acid sequence is highly repetitive or not) or mixtures of probes. The assays are carried out at room temperature to 100° C. but are typically carried out in the range of 37° C. to 80° C.

Semiconductor Nanocrystals as Detection Reagents in Signal Amplification Assays

In yet another embodiment of the invention, a method is disclosed for using semiconductor nanocrystals as a signal-generating label and semiconductor nanocrystal conjugates as the detection reagent in signal amplification assay formats. This type of signal amplification provides several advantages over currently employed methods for detecting the signal in signal-amplification assays. Among these advantages is the ability to detect multiple analytes in the same sample simultaneously with high sensitivity.

Semiconductor nanocrystals of one or more colors are individually conjugated to distinct molecules (a "semiconductor nanocrystal-conjugate") that specifically recognize an amplification complex generated in response to the presence of an analyte in a sample. A semiconductor nanocrystal-conjugate can be, for example, the label in 1) a DNA hybridization assay, (see Example 10), or 2) a biotin/avidin-layered amplification assay (see Example 11). The detection system is a device capable of measuring and distinguishing the wavelength of light emitted from semiconductor nanocrystals of one or more colors.

Semiconductor Nanocrystals for use in Multiplexed, Single Tube Assays

In still another embodiment of the invention, an HTS assay using semiconductor nanocrystals as multiplexed detection reagents is provided. Semiconductor nanocrystals of a particular color are conjugated by one of the techniques described in Bruchez et al. supra, Bruchez, supra, Chan et al., supra, or by any technique known in the art for attaching or conjugating proteins, nucleic acids, and the like. See, e.g., Hermanson (1996) *Bioconjugate Techniques* (Academic Press).

The HTS assay is performed in the presence of various concentrations of a candidate compound. The semiconductor nanocrystal emission is monitored as an indication of the effect of the candidate compound on the assay system. This technique is amenable to any of the conventional techniques with the exception of chemiluminscence. For example, fluorescence reading using a semiconductor nanocrystal-conjugated ligand or receptor to monitor binding thereof to a bead-bound receptor or ligand, respectively, may be used as a flexible format to measure the semiconductor nanocrystal emission associated with the beads. The measure of semiconductor nanocrystal emission associated with the beads can be a function of the concentration of candidate compound and, thus, of the effect of the candidate compound on the system. In addition, semiconductor nanocrystals can be used as a multicolor scintillant to detect the binding of a radiolabeled ligand or receptor with a semiconductor nanocrystal-conjugated receptor or ligand, respectively. A decrease in scintillation would be one result of inhibition by the candidate compound of the ligand-receptor pair binding.

Semiconductor Nanocrystals for use in High-throughput Sequence Analyses

Semiconductor nanocrystals conjugated to nucleic acids may be used in high-throughput DNA sequencing and DNA fragment analysis. To describe these sequencing reactions briefly, four reactions are performed to determine the positions of the four nucleotide bases within a DNA sequence. Using a DNA sample as a template, a chain of DNA is synthesized from a pool of nucleotides containing the four deoxynucleotides and one additional dideoxynucleotide. For example, in the adenine sequencing reaction, DNA is synthesized from a mixture that includes all four deoxynucleotides (DATP, dGTP, dCTP, dTTP) plus dideoxyadenosine triphosphate (ddATP). The enzyme DNA polymerase will synthesize the new chain of DNA by linking dNTPs. Occasionally DNA polymerase will incorporate a ddATP instead of a dATP. The ddATP in the nascent chain will then terminate the synthesis of that chain of DNA due to the lack of the 3' hydroxyl group as a connection to the next dNTP. Thus the DNA products from the adenine sequencing reaction will be a heterogeneous mixture of DNA that vary in length with each chain terminated at a position corresponding to adenine.

The four DNA sequencing reactions are resolved by size by polyacrylamide gel electrophoresis. With singly radiolabeled ($^{32}$P or $^{35}$S) DNA, the four reactions are loaded into four individual lanes. The resolved products of differing sizes result in a pattern of bands that indicate the identity of a base at each nucleotide position. This pattern across the four lanes can be read like a simple code corresponding to the nucleotide base sequence of the DNA template. With fluorescent dideoxynucleotides, samples containing all four dideoxynucleotide chain-terminating reactions can be loaded into a single lane. Resolution of the four dideoxynucleotide reactions is possible because of the different fluorescent labels for each sample. For example, ddATP can be conjugated with a green fluorescent tag. The other three ddNTP (dideoxynucleotide triphosphate) are tagged with three different fluorescent colors. Thus, each chain-terminating ddNTP is coded with a different color. When all four reactions are resolved in one lane on a DNA sequencing gel, the result is one ladder of bands having four different colors. Each fluorescent color corresponds to the identity of the nucleotide base and can be easily analyzed by automated systems.

However as previously discussed, multiple light sources are needed for excitation of the four different fluorescent organic dye markers. The use of semiconductor nanocrystals as the fluorescent tags for each dideoxynucleotide chain-terminating reaction simplifies the automation of high-throughput DNA sequencing since only a single light source is needed to excite all four fluorescent tags. In addition, multiplexing with semiconductor nanocrystals permits multiple sequencing reactions to be conducted and analyzed simultaneously, thereby further increasing the throughput of the assay.

In PCR (polymerase chain reaction)-based DNA typing and identification, short tandem repeat (STR) loci in the human genome are amplified by PCR using primers that are labeled with fluorescent tags. The size of these loci can differ or can coincide from person to person, or from individual subject to individual subject, and depends on genetic differences in the population. Usually multiple loci are examined. Any locus that shows a size difference with another sample conclusively indicates that the two samples are derived from two different individuals. However, demonstrating that two samples originate from the same individual is less conclusive. Unlike fingerprint patterns, the size of STR loci can coincide between two individuals. However, the statistical probability of multiple loci coinciding in size between two individuals decreases as the number of loci examined is increased. Using conventional organic fluorescent dyes, a limitation to the number of samples resolved in a single lane (and thus high-throughput) is the number of the fluorescent tags available and the resolution of the emission spectra. Increasing the resolution of the fluorescent tags thus would increase the capacity of the number of loci tested per lane on a gel.

Semiconductor Nanocrystals as Detection Reagents in DNA-based Assays

In still further embodiments of the invention, semiconductor nanocrystals can be used in other hybridization formats, sequence specific extension and oligo ligation assays, for detecting the presence/absence of specific DNA target sequences.

DNA Hybridization:

The single strands within DNA helices are held together by virtue of the hydrogen bonds between complementary bases in each strand. When double-stranded DNA ("dsDNA") is subjected to physical/chemical conditions which disrupt hydrogen bonds (i.e., denature the DNA), the strands separate into single-stranded ("ssDNA") molecules. When a mixture of different dsDNA molecules is denatured and then returned to conditions in which hydrogen bonds between complementary bases can reform, many of the complementary ssDNA strands will "find" each other and hybridize (reanneal) to form the original dsDNA molecules. The process of nucleic acid hybridization serves as the basis for countless diagnostic tests: e.g., Dot Blots, Southern Blots, Northern Blots, and FISH Analysis.

Denaturation:

DNA duplexes are held together by hydrogen bonds between complementary base pairs as well as by hydrophobic interactions between the stacked bases. These associations can be disrupted (i.e., DNA can be denatured, or "melted") by raising the temperature, decreasing the salt concentration, increasing the alkalinity, or by adding various organic reagents. Since G-C base pairs form three hydrogen bonds, whereas A-T base pairs form two hydrogen bonds, A/T-rich DNA helices melt (denature) at lower temperatures and/or higher salt concentrations than G/C-rich sequences. The amount of dsDNA that has become denatured (single-stranded, ssDNA) can be determined by a variety of physical and chemical means. The temperature at which 50% of the total base pairs within the dsDNA molecules in a solution have become disrupted is called the melting temperature (Tm).

Renaturation ("reannealing," "hybridization"):

The stability of nucleic acid hybrids is dependent on environmental conditions; two of the most important of which are temperature and salt concentration. In general, DNA duplexes are more stable at lower temperatures and higher salt concentrations. When denatured DNA is cooled or subjected to higher salt concentrations, it will spontaneously renature. Under ideal renaturation conditions and given sufficient time, mixtures of single-stranded fragments of DNA will reassociate (hybridize) with their complementary sequences. This property of nucleic acids is the basis upon which the assays disclosed herein are founded.

Stringency of Hybridization:

When ssDNA molecules form hybrids, the base sequence complementarity of the two strands does not have to be perfect. Poorly matched hybrids (i.e. hybrids in which only some of the nucleotides in each strand are aligned with their complementary bases so as to be able to form hydrogen bonds) can form at low temperatures, but as the temperature is raised (or the salt concentration lowered) the complementary base-paired regions within the poorer hybrids dissociate due to the fact that there is not enough total hydrogen bond formation within the entire duplex molecule to hold the two strands together under the new environmental conditions. The temperature and/or salt concentrations may be changed progressively so as to create conditions where an increasing percentage of complementary base pair matches is required in order for hybrid duplexes to remain intact. Eventually, a set of conditions will be reached at which only perfect hybrids can exist as duplexes. Above this stringency level, even perfectly matched duplexes will dissociate. The stringency conditions for each unique fragment of dsDNA in a mixture of DNA depends on its unique base pair composition. The degree to which hybridization conditions require perfect base pair complementarity for hybrid duplexes to persist is referred to as the "stringency of hybridization." Low stringency conditions are those which permit the formation of duplex molecules having some degree of mismatched bases. High stringency conditions are those which permit only near-perfect base pair-matched duplex molecules to persist. Manipulation of stringency conditions is key to the optimization of sequence specific assays.

Nucleic Acid Probes:

For each of the assay procedures described it is necessary to have one or more nucleic acid fragments that have been labeled with semiconductor nanocrystals, so that when they bind to the target DNA sequence their presence can be easily detected. Probes can consist of many nucleic acid types, depending on subtle aspects of the detection method and sample to be detected. They may be single-stranded or denatured double-stranded DNA or RNA. Probes of dozens to several hundred bases long can be artificially synthesized using oligonucleotide synthesizing machines, or they may be derived from various types of DNA cloning. The critical aspects are that the probe must contain a nucleic acid strand that is at least partially complementary to the target sequence to be detected, and the probe must be labeled with the semiconductor nanocrystals of the invention so that its presence can be visualized.

Semiconductor Nanocrystals for use in Spectral Karyotyping

Spectral karyotyping is a FISH technique used on metaphase preparations of chromosomes. See, e.g., Schrock et al. (1996) *Science* 273:494–497; and Macville et al. (1997) *Histochem. Cell. Biol.* 108:299–305. In spectral karyotyping and fluorescence in-situ hybridization (FISH) measurements, chromosomes are stained using combinations of dyes at different wavelengths and ratios. This acts to "barcode" different chromosomes for detection. For example, chromosome analysis is typically done by staining (e.g., Giesma stain). In a similar way, semiconductor nanocrystals can be used to barcode chromosomes using the techniques described above. In particular, as explained above, an arbitrary number of codes can be generated without the need to control the intensity of any spectral peak within the code. In this case, DNA probes are labeled with semiconductor nanocrystals that emit different colors to "paint" different chromosomes. Since the chromosomes are spatially separated during spectral karyotyping measurements, a barcoding system can be used to label each chromosome. The chromosomes act as the solid support for the coding semiconductor nanocrystal. By using this type of coding system, it is possible to generate an arbitrary number (more than 48) of unambiguous codes for spectral karyotyping.

In addition to barcoding entire chromosomes, it is also possible to barcode sections of a chromosome. In this way, this technique can replace traditional chromosome staining. Normally stains are used to label different spatially distinct regions of a chromosome. Different colors are used to stain different regions. With semiconductor nanocrystals, different sections on each chromosome can be painted with different barcodes. In this case, the spatial locations on the chromosome act as the substrate for different codes. This allows a very large number of regions to be labeled simultaneously.

Semiconductor nanocrystal-labeled probes for chromosome painting can be generated using techniques well known in the art, such as, but not limited to, micro-dissected PCR DNA or cloned DNAs (eg. from YACS, BACS, PACs etc.).

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Reagents for use in the following examples may be purchased from commercial sources, and used according to the manufacturers' directions. In the cloning of DNA fragments, except where noted, all DNA manipulations are done according to standard procedures. See, e.g., Sambrook et al., supra. Restriction enzymes, T4 DNA ligase, *E. coli*, DNA polymerase I, Klenow fragment, and other biological reagents are purchased from commercial suppliers and used according to the manufacturers' directions.

For the following examples, water-soluble core-shell nanocrystals are synthesized as described in Bruchez et al. (1998) *Science* 281:2013–2016. Affinity molecules are linked directly or indirectly to a semiconductor nanocrystal using chemical techniques well known in the art. See, e.g., U.S. Pat. No. 5,990,479 to Alivisatos et al; Bruchez et al. (1998) supra; and Chan et al. (1998) *Science* 281:2016–2018; Haugland, supra; and Hermanson "Bioconjugate Techniques" (Academic Press, NY).

EXAMPLE 1

Sandwich QISA

This example describes a sandwich QISA in which an analyte-specific antibody, or a plurality of different analyte-specific antibodies each of which is capable of specifically recognizing and binding to a distinct analyte, are immobilized on a solid support and analytes bound thereto are detected using one or a plurality of semiconductor nanocrystal/analyte-specific antibody conjugates.

A. A primary antibody (species 1 as illustrated in FIG. 1A) specific for the analyte to be detected in the sample is immobilized on a solid support, e.g., a well of a 96-well plate, using well-established techniques. The concentration of support-bound primary antibody is selected to be appropriate for the assay (1 ng/ml to 10 mg/ml). Optionally, the support is washed to remove unbound antibody.

Any portion of the solid support to which no antibody is bound is treated with an agent to reduce nonspecific binding thereto, e.g., 1% BSA+1% antibody species 2 antiserum (e.g., an antibody that is distinct from the first capturing antibody species) in phosphate-buffered saline (PBS). Optionally, the support is washed to remove excess blocking agent.

A sample containing or suspected of containing the analyte of interest is added to the treated solid support and incubated for a time (30 seconds to 48 hours) sufficient to bind the analyte to the primary antibody. Optionally, the support is again washed to remove nonspecific and unbound analyte molecules in the sample.

A secondary antibody (species 3 distinct from the primary antibody) conjugated to a single population of the same composition of semiconductor nanocrystals is added at a known concentration (1 ng/ml to 10 mg/ml) and incubated for a time (30 seconds to 48 hours) sufficient to bind the secondary antibody to the support-bound analyte. Optionally, the support is washed to remove unbound semiconductor nanocrystal-conjugated secondary antibody.

The results of assay are determined by measuring the intensity of light emitted from the semiconductor nanocrystals specifically bound to the solid support at wavelengths corresponding to the semiconductor nanocrystals component of the conjugate.

In particular, a QISA was performed by coating the wells of a 96-well plate with 10 μg/ml of rabbit IgG in PBS. After coating, the plate was washed and unbound sites were blocked with BSA. The plates were blocked for one hour at room temperature prior to washing and concentrations of biotinylated goat anti-rabbit IgG ranging from 0.1 nM to 100 nM (in PBS) were added. This was incubated in the wells for one hour at room temperature and then washed. 100 nM nanocrystal conjugates (streptavidin conjugates) were added which had an emission peak at 580 nm. The nanocrystal conjugates were incubated in the wells for one hour at room temperature and then washed. The plate was read on a Molecular Dynamics spectramax Gemini plate reader.

Figure 2:
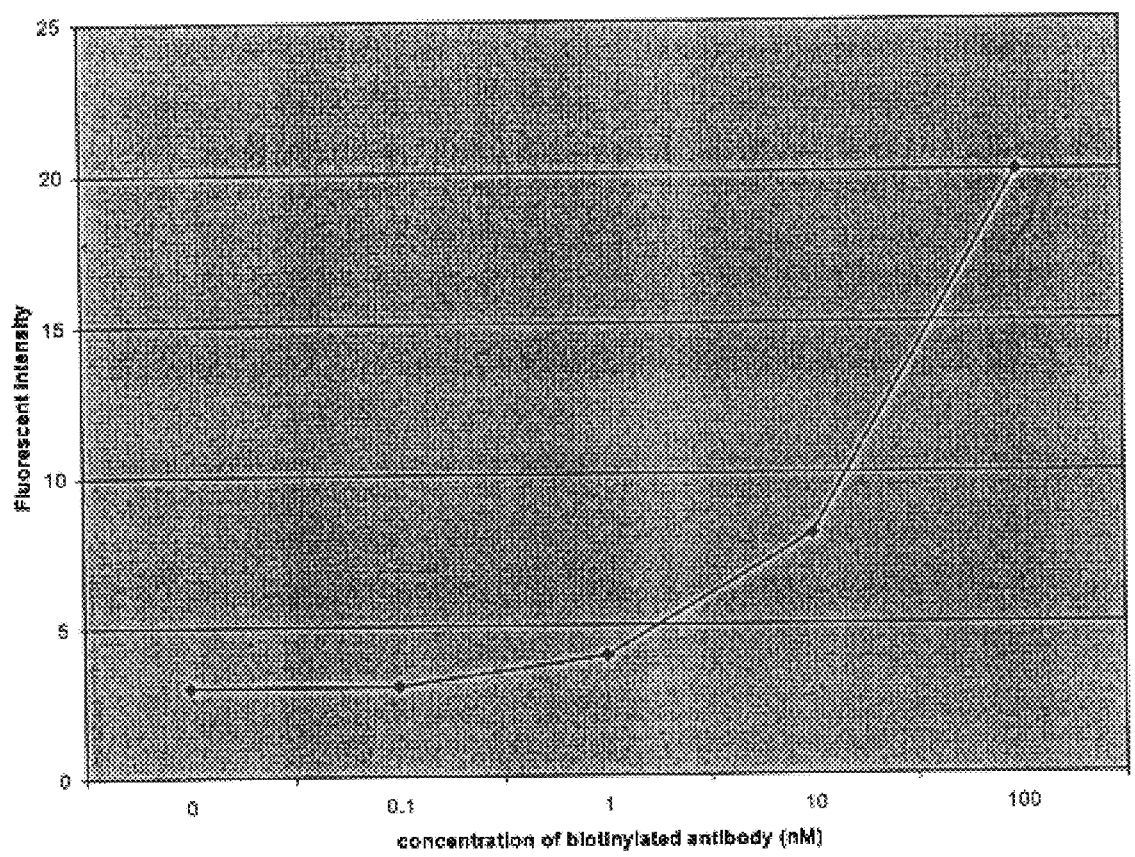
FIG. 2 shows the results of a QISA performed on a 96-well plate and read in a standard fluorescent plate reader, as described in Example 1A.

Results are shown in FIG. 2. As can be seen, fluorescent intensity increased with the concentration of biotinylated antibody used, demonstrating the usefulness of semiconductor nanocrystals in this context.

B. A sample can be analyzed simultaneously for the presence of more than one analyte in a single assay using a sandwich QISA as disclosed herein. A species of primary antibody capable of recognizing and specifically binding to one of each of the analytes of interest is bound to the solid support, the support is, optionally, washed, blocked and washed again, as described above. The sample is then added to the support and incubated for a time sufficient for each analyte to be recognized by and bind to its corresponding primary antibody. The support is, optionally, washed to remove unbound sample. A plurality of distinct secondary antibodies, each of which is capable of recognizing and binding to one of each of the analytes of interest and is conjugated to a distinct species of a semiconductor nanocrystal. Each distinct species of a semiconductor nanocrystal has distinctly detectable emission properties The support-bound semiconductor nanocrystal-antibody conjugates are simultaneously irradiated with blue light and the plurality of emission wavelengths corresponding to each species of semiconductor nanocrystal is monitored using an appropriate apparatus.

EXAMPLE 2

Direct Capture QISA

This example describes a direct capture QISA in which a sample containing or suspected of containing an analyte of interest or a plurality of different analytes of interest, is adsorbed onto a solid support and adsorbed analytes are detected using one or a plurality of semiconductor nanocrystal/analyte-specific conjugates, respectively.

A sample is adsorbed onto a solid support using well-established techniques for a time sufficient to effect adsorption (30 seconds to 48 hours). Optionally, the support is washed to remove unbound molecules. Nonspecific binding is minimized by treating the solid support to which sample has been adsorbed with an appropriate blocking agent, e.g., 1% BSA+1% serum (same species as primary antibody) in PBS. The support is again, optionally, washed to remove excess blocking agent, For detecting a single analyte, analyte-specific antibody conjugated to a single population of the same composition of semiconductor nanocrystals is added at a known concentration (1 ng/ml to 10 mg/ml) and incubated with the sample-adsorbed solid support for a time sufficient for the antibody to recognize and bind to its corresponding antibody (30 seconds to 48 hours). The support is, optionally, washed to remove unbound semiconductor nanocrystal-conjugated antibody.

Results of the assay are determined by measuring the intensity of light emitted at a wavelength that correspond to the semiconductor nanocrystal in the conjugate.

In a manner similar to that described in Example 1B, the direct capture QISA can be adapted to detect multiple analytes in a single sample by using a plurality of primary antibody species, each of which is conjugated to a semiconductor nanocrystal with distinctly detectable emission properties. The support-bound semiconductor nanocrystal-antibody conjugates are simultaneously irradiated with blue light and the plurality of emission wavelengths corresponding to each semiconductor nanocrystal is detected using an appropriate apparatus.

EXAMPLE 3

Fluid-Phase QISA

This example describes a fluid-phase QISA in which a fluid-phase sample containing or suspected of containing an analyte of interest or a plurality of different analytes of interest, is adsorbed onto a solid-phase substrate and adsorbed analytes are detected using one or a plurality of semiconductor nanocrystal/analyte-specific antibody conjugates.

A sample containing or suspected of containing analyte is adsorbed onto, for example, latex microspheres (see, e.g., Bangs Laboratories, Inc., TechNote#25) by incubating the microspheres with the sample for an appropriate amount of time (30 seconds to 48 hours). Optionally, the microspheres are washed, e.g., by centrifugation, to remove unbound sample. Microspheres to which analyte have been adsorbed are incubated with semiconductor nanocrystal-conjugated analyte-specific antibody (1 ng/ml to 10 mg/ml) for a period of time sufficient to allow binding of the antibody to the adsorbed analyte (30 seconds 48 hours). Optionally, the microspheres are washed to remove unbound semiconductor nanocrystal-conjugated antibodies.

The amount of semiconductor nanocrystal fluorescence associated with the microspheres can be detected using flow cytometry or a static fluorimeter capable of distinguishing the different spectrum of emissions from the semiconductor nanocrystal conjugates.

In a manner similar to that described in Example 1B, the fluid-phase QISA can be adapted to detect multiple analytes in a single sample by using a plurality of primary antibody species, each of which is conjugated to a semiconductor nanocrystal with distinctly detectable emission properties. The support-bound semiconductor nanocrystal-antibody conjugates are irradiated with blue light and the plurality of emission wavelengths corresponding to each semiconductor nanocrystal is detected using flow cytometry or a static fluorimeter as described above.

EXAMPLE 4

Fluid-Phase QISA

This example describes a fluid-phase QISA in which a fluid-phase sample containing or suspected of containing an analyte of interest or a plurality of different analytes of interest, is incubated with and bound to a primary antibody, or a plurality of primary antibodies capable of specifically recognizing and binding to an analyte. The primary antibody is immobilized on a microsphere. Bound analyte or analytes are detected using one or a plurality of semiconductor nanocrystal/analyte-specific antibody conjugates.

A primary polyclonal or monoclonal antibody (species 1) specific for the analyte to be detected in the sample is immobilized onto microspheres using well-established techniques. The concentration of primary antibody should be appropriate for the assay (1 ng/ml to 10 mg/ml), as described in Example 1. Optionally, the microspheres are washed to remove unbound primary antibody.

A sample containing or suspected of containing an analyte is incubated with microspheres to which have been conjugated an analyte-specific antibody for a period of time (30 seconds to 48 hours) sufficient to effect binding of an analyte to its respective antibody. Optionally, the microspheres are washed to remove unbound sample and/or analyte.

Primary antibody-microsphere conjugates which have been incubated with the sample are then incubated with a semiconductor nanocrystal/analyte-specific secondary antibody conjugates at a concentration (1 ng/ml to 10 mg/ml) and for a period of time (30 seconds to 48 hours) sufficient to effect binding of the semiconductor nanocrystal-conjugated to the microsphere-immobilized analyte. Optionally, the microspheres are washed to remove unbound semiconductor nanocrystal-conjugated antibodies.

The amount of semiconductor nanocrystal fluorescence associated with the microspheres can be detected using flow cytometry or a static fluorimeter capable of distinguishing the different spectrum of emissions from the semiconductor nanocrystal conjugates.

In a manner similar to that described in Example 3, the fluid-phase QISA can be adapted to detect multiple analytes in a single sample by using a plurality of primary antibody species, each of which is specific for a preselected analyte, conjugated to a microphere, and a plurality of semiconductor nanocrystal/analyte-specific secondary antibody conjugates, in which each conjugate contains a semiconductor nanocrystal having distinctly detectable emission properties. The support-bound semiconductor nanocrystal-antibody conjugates are irradiated with blue light and the plurality of emission wavelengths corresponding to each semiconductor nanocrystal is detected using flow cytometry or a static fluorimeter as described above.

EXAMPLE 5

DNA-based FISH Assay

The specimen for FISH assay is prepared using various published methods depending on the specimen type, as described above.

A. Double-stranded specimen DNA and semiconductor nanocrystal-FISH probe(s) can be denatured together or separately to their single-stranded form. Denaturation of semiconductor nanocrystal-FISH probes consisting of synthetic oligonucleotides without secondary structure is not necessary. The specimen and probes in single-stranded form are allowed to hybridize to their complimentary sequence in hybridization buffer optionally containing blocking DNA (5 minutes to overnight at 25° C.–70° C.). The excess semiconductor nanocrystal-FISH probes are removed using a series of stringent washes. (e.g., 0.4×SSC to 2×SSC with or without formamide at 25° C.–72° C.). Optionally, the specimen is air dried and counterstained to localize the nuclei.

More particularly, semiconductor nanocrystal-FISH probe(s) is added to the hybridization mix containing 50% formamide, 10% dextran sulphate, 1×SSC (saline citrate), 3 μg Cot1 DNA. The probe mixture is deposited on the slide and a coverslip is placed on the probe. The slide is placed on a hot plate for 3 minutes at 72° C. to denature the specimen and probe DNA. The specimen and probes in single-stranded form are allowed to hybridize to their complimentary sequence for 5 minutes to overnight at 25° C. to 45° C. The excess semiconductor nanocrystal-FISH probes are removed by washing the slide in 2×SSC, 0.3% NP-40 for 2 minutes. The specimen is air dried and counterstained to localize the nuclei.

The fluorescence signals of the semiconductor nanocrystal-FISH probes is viewed under an epifluorescence microscope. Alternatively, the signals are measured using a laser detector.

B. Whole Chromosome Paints:

Human chromosomes 1, 2, and 3 were each microdissected, PCR amplified and labeled with biotin-dUTP as described in Meltzer et al. (1992) *Mat. Genet.* 1:24–28. Slides with metaphase spreads from peripheral blood lymphocytes were prepared using conventional cytogenetics techniques and denatured for 2 minutes at 72° C. in 70% formamide, 2×SSC (saline citrate). The slides were then dehydrated 1 minute each with a series of 70%, 85% and 100% ethanol and air-dried. Hybridization mixture (10 ng/μl DNA of each whole chromosome probe in 50% formamide, 10% dextran sulphate, 1×SSC, 3 μg Cot1 DNA) was denatured for 5 minutes at 72° C. and placed on the slides. A cover slip was placed on each slide and sealed with rubber cement. The slides were incubated at 37° C. overnight in a humidified chamber. After hybridization, the excess probes were washed away three times with 2×SSC, 50% formamide at 42° C. for 3 minutes each, followed by a rinse with 2×SSC at ambient temperature for 3 minutes. The slides were then blocked with 4×SSC, 0.1% Tween 20, 1% BSA (Bovine Serum Albumin) for 30 minutes to prevent nonspecific binding. Finally the slides were incubated with 40 nM of 630 nm semiconductor nanocrystal-streptavidin in PBS (Phosphate buffered saline), 1% BSA, 10 mM $MgCl_2$ at ambient temperature for 1 hour. The excess semiconductor nanocrystal-streptavidin and salts were removed by rinsing the slides in PBS and in 10 mM Phosphate buffer. The slides were then air dried and examined with a fluorescence microscope.

Chromosome pairs 1, 2 and 3 were readily visualized using the fluorescence microscope, demonstrating the utility of using semiconductor nanocrystals in this context.

C. Fiber FISH

Semiconductor nanocrystals were used in a Fiber FISH format essentially as described by Heiskanen et al. (1994) *Biotechniques* 17:928–933; and Heiskanen et al. (1995) *Genomics* 30:31–36. In particular, a 10 kb DNA probe was labeled by nick-translation using biotin-11-dUTP (Sigma Chemical). Fiber FISH slides were prepared as described in Heiskanen et al., supra. The slides were denatured in 70% formamide, 2×SSC at 72° C. for 4 minutes followed by dehydration with a series of 70%, 85% and 100% ethanol. Biotin labeled DNA probes 2.5–7.5 ng/μl were added to hybridization mix containing 50% formamide, 10% dextran sulfate, 2×SSC, 0.2 μg/μl herring sperm DNA, 0.25 μg/μl Cot-1 DNA. The mixture was placed on slides, a coverslip was placed over each slide and hybridized overnight at 37° C. in a humidified chamber. Excess probes were removed by washing the slides three times with 50% formamide, 2×SSC for 5 minutes each, two times with 2×SSC for 5 minutes each and a final wash in 0.5×SSC for 5 minute all at 45° C. Slides were incubated in 5% BSA, 4×SSC, 0.05% Tween 20 for 15 minute at 37° C. to block nonspecific binding. Biotinylated probes were detected by incubating in 40 nM semiconductor nanocrystal-streptavidin in PBS, 1% BSA and 10 mM $MgCl_2$, followed by biotinylated anti avidin antibody and another layer of semiconductor nanocrystal-streptavidin conjugate. The slides were rinsed in PBS, stained with 5 μg/ml DAPI (Sigma Chemical) and examined in a fluorescence microscope.

The DNA probes were readily visualized using a fluorescence microscope, demonstrating the utility of semiconductor nanocrystals for physical mapping positional cloning.

EXAMPLE 6

RNA-based FISH Assay

The specimen for FISH assay is prepared using various published methods depending on the specimen type, as described above.

Semiconductor nanocrystal-FISH probe(s) for RNA are denatured to their single-stranded form. The specimen and probes in single-stranded form are allowed to hybridized to their complimentary sequence in hybridization buffer optionally containing blocking DNA (e.g., 5 minutes to overnight at 25° C.–70° C.).

The excess semiconductor nanocrystal-FISH probes are removed using a series of stringent washes (e.g. 0.4×SSC to 2×SSC with or without formamide at 25° C.–72° C.). Optionally, the specimen are air dried and counterstained to localize the nuclei.

The fluorescence signals of the semiconductor nanocrystal-FISH probes are viewed under an epi-fluorescence microscope. Alternatively, the signals can be measured using a laser detector.

In particular, synthetic oligonucleotide probes directed against a certain mRNA are labeled with semiconductor nanocrystals at the 3' or 5' end. The probes are added to the hybridization mix containing 50% formamide, 10% dextran sulphate, 1% sarkosyl, 0.02 M sodium phosphate, 4×SSC, 1×Denhardt's solution and 10 mg/ml ssDNA. The probe mixture is added to the specimen, a coverslip is placed over the probe, and the probe and mRNA are allowed to hybridized for 16–20 hours at 42° C. in a humidified chamber. After hybridization, the excess probes are removed by washing several times in 1×SSC at 55° C. and air-dried. The slides are then examined under a fluorescence microscope.

EXAMPLE 7

Multiplexed DNA- and RNA-based FISH Assay

The specimen for FISH assay is prepared using various published methods depending on the specimen type, as described above.

Double-stranded specimen DNA and semiconductor nanocrystal-FISH probe(s) can be denatured together or separately to their single-stranded form.

The specimen and semiconductor nanocrystal-FISH probes for both RNA and DNA in single-stranded form are allowed to their complimentary sequence in hybridization buffer optionally containing blocking DNA (5 minutes to overnight at 25° C.–70° C.).

The excess semiconductor nanocrystal-FISH probes for RNA and DNA are removed using a series of stringent washes (e.g., 0.4×SSC to 2×SSC with or without formamide at 37° C.–72° C.).

A flow cytometer or other similar detector can be used to scan the specimens to detect the fluorescence from the semiconductor nanocrystal RNA probe and the cell's DNA fluorescence signals are detected simultaneously. Alternatively, the rare cells are sorted aside for further DNA analysis using a microscope.

For example, semiconductor nanocrystal-FISH probes for DNA and RNA are added to the hybridization mix containing 50% formamide, 10% dextran sulphate, 1–4×SSC (saline citrate), 3 μg Cot1 DNA, 10 mg/ml ssDNA. The probe mixture is deposited on the slide and a coverslip is placed on the probe. The slide is placed on a hot plate for 3 minutes at 72° C. to denature the specimen and probe DNA. The specimen and probes in single-stranded form are allowed to hybridize to their complimentary sequence overnight at 25° C. to 45° C. After hybridization, the excess probes are removed by washing several times in 1×SSC at 55° C. and air-dried. The specimen is counterstained to localize the nuclei.

The fluorescence signals of the semiconductor nanocrystal-FISH probes are viewed under an epi-fluorescence microscope. Alternatively, the signals are measured using a laser detector.

EXAMPLE 8

Immunostaining and FISH Assays

Specimen cells are labeled with optimized concentration of semiconductor nanocrystals-antibody(ies) or antibody with other dye label specific to cell surface protein of interest (e.g. anti-CD4 or anti CD14).

The cells are fixed and permeabilized by addition of reagents such as PERMEAFIX® (Ortho Diagnostics). After incubation, the cells are pelleted and washed.

The cell pellet is resuspended for FISH assay with hybridization buffer containing single-strand semiconductor nanocrystal-RNA probes optionally containing blocking DNA. The mixture is allowed to hybridized to their complimentary sequence (5 minutes to overnight at 25° C.–70° C.).

The excess semiconductor nanocrystal-FISH probes are removed using a series of stringent washes (e.g., 0.4×SSC to 2×SSC with or without formamide at 37° C.–72° C.).

A flow cytometer or other similar detector can be used to scan the specimens to sort and/or to detect the surface immunofluorescence and fluorescence from the semiconductor nanocrystal RNA probe simultaneously.

In particular, specimen cells are fixed and permeabilized by addition of reagents such as Penneafix (Ortho Diagnostics). After incubation the cells are pelleted and washed. The cell pellet is resuspended for FISH assay in hybridization buffer. The hybridization mixture contains semiconductor nanocrystal-FISH probes for DNA or RNA, 50% formamide, 10% dextran sulphate, 14×SSC, 3 μg Cot1 DNA (for DNA probes) and or 10 mg/ml ssDNA (for RNA probes). The mixture is allowed to denatured for 2 minutes at 72° C. and hybridized overnight at 25° C.–45° C. The excess FISH probes are removed by washing several times in 1×SSC at 55° C. Monoclonal antibody from mouse to a protein of interest is used to bind the specimen cells using standard immunohistochemistry procedures. The excess antibody is removed, the specimen is incubated with semiconductor nanocrystal-labeled anti-mouse IgG. The excess semiconductor nanocrystal anti-mouse IgG is removed and the specimen cells can be examined under a fluorescence microscope. Alternatively, a flow cytometer or other similar detector can be used to scan the specimens to sort and/or to detect the fluorescence from the semiconductor nanocrystal-FISH probes and semiconductor nanocrystal-labeled antibody.

EXAMPLE 9

FISH Assay of Amplified Specimen DNA

Specimen cells were fixed and permeabilized by addition of reagents such as Permeafix (Ortho Diagnostics). After incubation the cells are pelleted and washed.

The cell pellet is resuspended with PCR reaction mixture along with optimized concentrations of dNTP and semiconductor nanocrystal dUTP, semiconductor nanocrystal-forward primer and semiconductor nanocrystal-reverse primer for DNA or RNA of interest, Taq polymerase and gelatin.

The DNA in the above reaction mixture is amplified in a thermocycler programmed for the specific conditions.

After in vitro amplification, cells are pelleted and resuspended in hybridization mix along with semiconductor nanocrystal-oligonucleotide probe directed against the specific amplified product and, optionally, blocking DNA to reduce background noise.

The product DNA is denatured and allowed to hybridized with the semiconductor nanocrystal-oligonucleotide probe (5 minutes to overnight at 25° C.–70° C.).

The excess semiconductor nanocrystal-oligonucleotide probes are removed using a series of stringent washes (e.g., 0.4×SSC to 2×SSC with or without formamide at 37° C.–72° C.).

A flow cytometer, or other similar detector, or epi fluorescence microscope is used to detect the fluorescence signals from the semiconductor nanocrystal-oligonucleotide probes.

EXAMPLE 10

Signal Amplification in a DNA Hybridization Assay

A unique DNA sequence is chosen as a capture probe and is designed to have a sequence complementary to a sequence in a capture extender oligonucleotide. This sequence can range from 10 to 25 nucleotides in length. This DNA capture probe sequence is chemically synthesized and purified.

The capture probe is conjugated to the surface of a well of a microtiter plate, using any one of a variety of standard chemical linkages and methods well known in the art. The analyte is immobilized on the microtiter support through one or more oligonucleotides (capture extenders) that have first and second complementary sequences. The first sequence is complementary to a sequence in the target analyte and the second sequence is complementary to a sequence in the support-bound capture probe. The capture extenders and the sample can be added to the assay simultaneously. Alternatively, the capture extender can be added and allowed to hybridize to the complementary sequence in the support-bound capture probe prior to addition of the sample. Hybridization is allowed to occur under conditions that favor hybridization for a period of time sufficient to effect hybridization of the capture extender to the capture probe and the target analyte to the capture extender. The assay format can be designed so that the target analyte will be immobilized to the solid support only if two capture extenders, in which the first complementary sequences thereof are complementary to distinct segments in the target analyte, hybridize to the target. In addition, the support-bound capture probe and the capture extenders can be designed so that the second complementary sequence in the capture extenders are complementary to distinct segments in a capture probe. Thus, in order to immobilize the target to the solid support, the second complementary sequences of two distinct capture extenders hybridize to distinct complementary sequences in a capture probe and the first complementary sequences of the capture extenders hybridized to distinct sequences in the target analyte.

After hybridization, an optional step is performed under appropriate stringency conditions to separate material not retained on the solid support.

One or more label extender oligonucleotide probes complementary to the analyte sequence is chosen. Each of these target probe oligonucleotides contains a second sequence segment substantially complementary to a nucleic acid sequence within an amplifier oligo. Hybridization is allowed to occur. After hybridization, a wash step is performed under appropriate stringency conditions.

The amplification oligo contains a sequence complementary to a portion of each target probe oligo and also contains a multiplicity of label probe sites. Hybridization is allowed to occur. After hybridization, a wash step is performed under appropriate stringency conditions.

Semiconductor nanocrystal-conjugated oligos which are complementary to the amplifier oligos are allowed to hybridize to the amplifier oligos. Hybridization is allowed to occur. After hybridization, a wash step is performed under appropriate stringency conditions.

Finally the well is scanned in a fluorimeter. The amount of light emitted at the excitation wavelength of the semiconductor nanocrystals is measured. Light emission at the detection wavelength is proportional to the amount of target nucleic acid present.

EXAMPLE 11

Signal Amplification in a Biotin/Avidin-Layered Amplification Assay

The sample is immobilized on a solid support by established techniques. Unbound sample is washed from the solid support.

A biotin-labeled antibody is reacted with an immobilized antigen, followed by appropriate washes. Biotin-conjugated semiconductor nanocrystals are mixed with avidin (or streptavidin) in specific ratios to form complexes consisting of multiple inter-linked avidin-semiconductor nanocrystal complexes with some free biotin-binding sites still available. An aliquot of this complex is added to the immobilized biotin-labeled antibody/antigen complex. Unbound complex is washed using appropriate conditions.

Result for assay is determined by measuring the intensity of light emitted at wavelengths that correspond to the semiconductor nanocrystals used.

EXAMPLE 12

Multiplexed Bead-Based Assay Using Multiple Semiconductor Nanocrystal-Ligand Receptor Pairs $5 \times 10^6$ 10 μm polystyrene-divinylbenzene, diaminododecane beads are rinsed with ethanol, then twice with phosphate buffered saline (PBS) with 0.05% $NaN_3$. They are then resuspended in 1 ml of this solution, and incubated for one hour sequentially with each of the following reagents, with two wash steps between each incubation: 50 μg/ml BSA-Biotin (Bovine serum albumin-biotinylated) in $PBS/NaN_3$, 50 μg/ml streptavidin in PBS/NaN3, 50 μg/ml of a biotinylated monoclonal antibody which specifically binds the noninteracting region of the receptors (e.g., MAb179), and 2 μg/ml of the purified extracellular domain of the receptor (e.g., IL-5).

Another $5 \times 10^6$ 10 μm polystyrene-divinylbenzene, diaminododecane beads are rinsed with ethanol, then twice with PBS with 0.05% $NaN_3$. They are then resuspended in 1 ml of this solution, and incubated for one hour sequentially with each of the following reagents, with two wash steps between each incubation: 50 μg/ml BSA-Biotin in $PBS/NaN_3$, 50 μg/ml streptavidin in $PBS/NaN_3$, 50 μg/ml of a biotinylated monoclonal antibody which specifically binds the noninteracting region of the receptors (e.g., MAb179), and 2 μg/ml of the purified extracellular domain of the receptor (e.g., IL-1).

$2 \times 10^6$ of each receptor bound bead are thoroughly mixed into a single tube. This suspension was distributed into 8 wells containing 5000 beads each. 5000 beads of each of the receptors (IL-1 and IL-5) are put into two further sets of 8 wells, as shown in FIG. 3.

IL-1 receptor-antagonist and IL-5 receptor antagonist are conjugated to red and green semiconductor nanocrystals using techniques previously described. These are prepared in a stock solution to 16 nM, then mixed in equal volumes with a dilution series (0, 1 nM, 10 nM, 100 nM, 1 μM, 10 μM, 100 μM, 1 mM) of a competing molecule. 50 μl of these solutions are added to each of the wells, each well 1–8 containing a unique concentration of the inhibitor (as above), each of the columns A–C (FIG. 3) having identical conditions and only different beads. After incubation, the beads from each well are transferred to tubes for flow cytometric analysis, though other analysis techniques may be preferable. The cytometer separates the beads into individual events, allowing the detection of two wavelengths of light (e.g. the fluorescence from the red and green semiconductor nanocrystals) simultaneously upon excitation with a 488 nm laser. In this assay, the ligand can inhibit one, both, or neither of the ligand-receptor pairs. If the inhibitor is ineffective for both systems, the results will be uniform across the concentration of inhibitor, and should vary very little from the control wells. When the inhibitor is effective in only one of these assays, for instance against IL-1 only, then the wells in column A have decreasing red fluorescence associated with the beads at higher inhibitor concentrations.

A plot of the relative fluorescence with respect to the standard as a function of concentration reveals the concentration at which the normal receptor-ligand pair binding is inhibited by 50% (this is known as the IC50). In contrast, the wells in column C (FIG. 3) are unaffected by the presence of the inhibitor at all concentrations. In the center lane, the true multiplexed assay is performed, and the results are seen as beads which fluoresce lower intensities of red at the higher concentrations (due to inhibition of binding), and beads which fluoresce with a homogeneous intensity of green (due to the lack of inhibition of the IL-5 interactions). Homogeneously stained green beads are present throughout each of the inhibition series of the red emitting beads.

This format has advantages over standard formats using dye molecules in that the number may be expanded significantly beyond two using a variety of different colors (and thus different size or composition) semiconductor nanocrystals, each conjugated to a unique receptor or ligand, in order to maximize the throughput in a single well. Furthermore, the fact that each and every scintillation event is due to a ligand-receptor pair formation (in the low concentration limit) makes this a very sensitive technique for which there are no standard multiplexing methods.

EXAMPLE 13

Use of Semiconductor Nanocrystals in a Homogeneous Scintillation Inhibition Assay When the semiconductor nanocrystals are brought within 1 μm of a radioactive nucleus, they can be made to emit light upon the decay of that nucleus, which produces high energy radiation, which is dissipated by the solvent, and can excite the semiconductor nanocrystals, causing them to emit light. In order to get the semiconductor nanocrystals to efficiently emit light, it is necessary to have the nucleus remain in close proximity. This can be accomplished through ligand-receptor interactions, where one is radiolabeled, and the other is conjugated to a semiconductor nanocrystal. This homogeneous assay format is advantageous in that it allows free association in solution of all the receptor-ligand pairs, each of which can be prepared to scintillate in a unique region of the spectrum. Semiconductor nanocrystals which emit in green, yellow, and red regions of the spectrum, and are well resolved spectrally are conjugated to three different ligands (receptor antagonists) to the IL-1, IL-5, and IL-12 receptors respectively. A solution is prepared which is 1 nM in each of these semiconductor nanocrystal-receptor antagonist conjugates. Aliquots are mixed with a concentration series of the inhibitor of interest, and brought to identical final volumes and concentrations of RA-semiconductor nanocrystals (0.75 nM each). Radiolabeled ($^3$H) IL-1, IL-5, and IL-12 receptor extracellular domains are prepared by proton exchange, as known in the art. A stock is prepared which contains 1 nM of all three of these tritiated proteins in phosphate buffered saline. This stock is added to result in a final concentration of each receptor of 0.001 nM, a large excess of ligand over receptor. Scintillation is seen only from semiconductor nanocrystals which are bound to receptor antagonist which is not inhibited by the candidate inhibitor. A lower signal is seen in the characteristic color when the inhibition is effective. These may be referenced to the control well without inhibitor.

Figure 4:
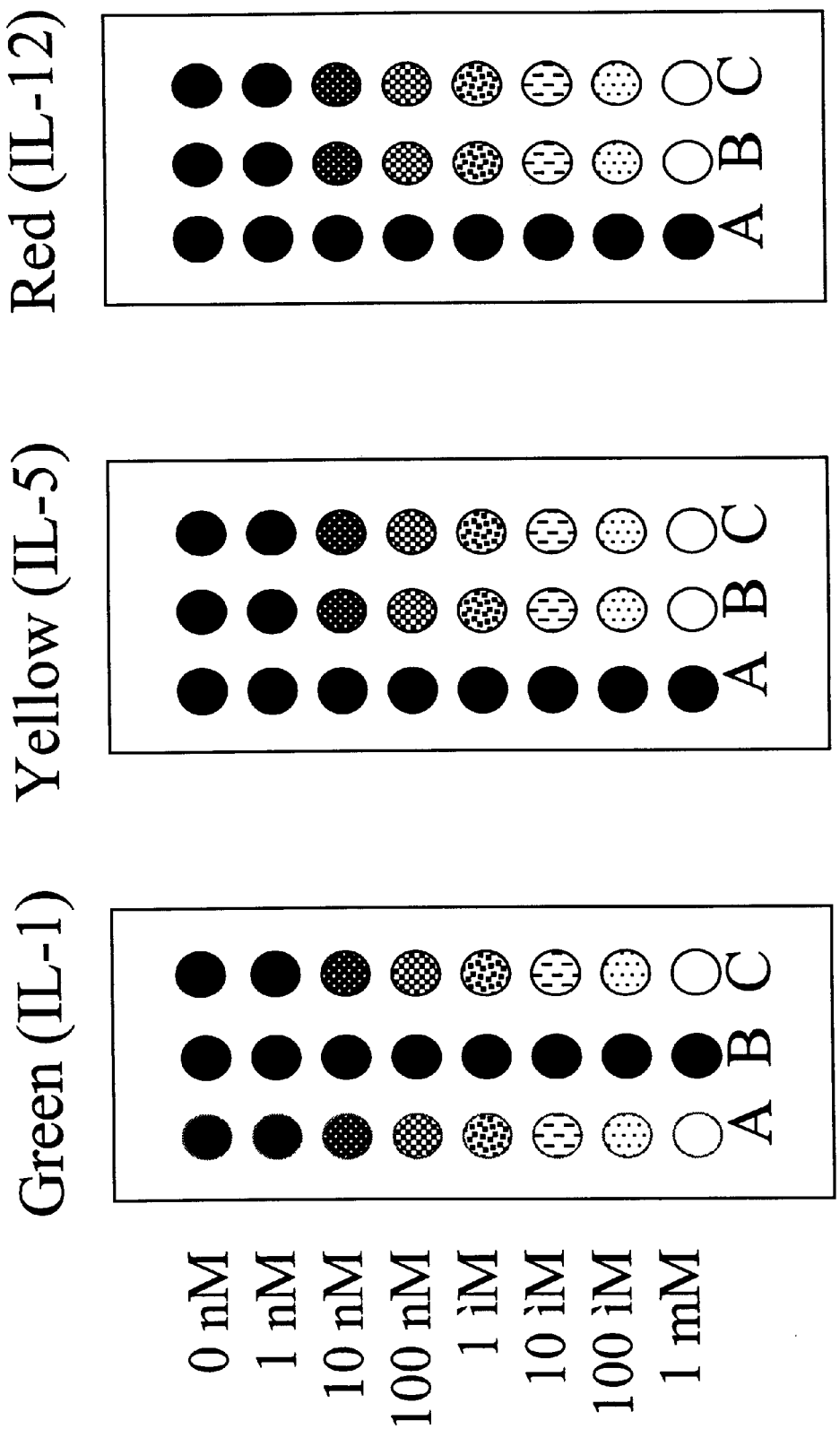
FIG. 4 is a representation of results that can be obtained when semiconductor nanocrystals are used in a homogeneous scintillation inhibition assay, as described in Example 13. In the Figure, lanes A, B and C contain different inhibitors.

Signal may be detected in a dark box with a camera mounted such that it can image the entire plate. All that is necessary is for the camera to integrate the collected light for a long period, as the scintillation is a low background technique. In addition, multiple filters can be used to separate the signal arising from each ligand-receptor pair. In FIG. 4, lanes A, B, and C contain different inhibitors, lane A for IL-1 only, lane B for IL-5 and IL-12, and lane C for all receptors.

The unique combination of colors which indicate inhibition will determine which receptors the candidate may be an appropriate drug for. One principal advantage of such a system is that it may be performed with as many ligands as one can produce spectrally resolved semiconductor nanocrystals. Since the range of 300 nm to 1.5 μm is available for semiconductor nanocrystal manufacture, well over 20 colors should be available for multiplexing in a homogeneous reaction format. Furthermore, the fact that each and every scintillation event is due to a ligand-receptor pair formation (in the low concentration limit), this is a very sensitive technique for which there are now no known techniques that are capable of multiplexing.

EXAMPLE 14

Hybridization Assays

Hybridization assays are a convenient method for determining the presence or absence of a specific DNA sequence in a sample. Semiconductor nanocrystals are used to 5' end label a pair of allele specific oligonucleotide primers. These primers are used in PCR or other DNA amplification reaction, such that the target sequence of interest is amplified, i.e., increased, in number. A sequence-specific oligonucleotide probe is synthesized, and is immobilized onto a surface to become a capture probe. The amplified target is applied to the surface, and allowed to hybridize under sufficiently stringent conditions of temperature and salt concentration. After hybridization, unbound material is washed away. The presence of semiconductor nanocrystals immobilized on the surface is detected by exciting at an allowed absorbance wavelength, and measuring at the semiconductor nanocrystal emission wavelength. The presence of a semiconductor nanocrystal emission on the surface is directly proportional to the amount of amplified target DNA present.

A. A DNA sequence complementary to the target sequence is chosen. This equence can range from 15 to 25 nucleotides in length. This DNA probe sequence is hemically synthesized and purified. The probe is conjugated to the surface of a well of microtiter plate, using any one of a variety of standard chemical linkages.

Two PCR primer sequences are selected, such that they specifically amplify a ortion of the target DNA sequence containing the region to be probed. The 5' end of each of the two primers is labeled with a semiconductor nanocrystal with peak emission at 525 nm. These two primers are used to amplify a defined portion of the target DNA in a standard PCR reaction. Since the semiconductor nanocrystal is conjugated to the primer, and the primer is extended to become the amplified target, the semiconductor nanocrystal is connected to the 5' end of the amplified target.

After the thermal cycling the target can be denatured or made single-stranded by heating it for two minutes at 95° C.

The hybridization is performed by adding 20 μl of the amplified target and 480 μl of 5xSSPE Buffer to the microtiter well coated with DNA probe, and incubating for 60 minutes at 37° C. After hybridization, a wash step under stringent conditions is performed by adding 500 μl of 3xSSPE, and incubating for 15 minutes at 37° C. The well is rinsed twice with water.

In places where the amplified DNA hybridized to the immobilized probe, the semiconductor nanocrystal with 525 emission is connected to the surface. The well is scanned in a fluorimeter. UV light is shone upon the well, and the amount of phosphorescence at 525 nm is measured. The presence of 525 nm emission indicates that the immobilized probe-captured semiconductor nanocrystal-labeled amplified target, and remained hybridized after the stringent wash and water rinse steps.

B. Three DNA sequences complementary to the three different target sequences are chosen. These sequences can range from 15 to 25 nucleotides in length. These three DNA probe sequences are chemically synthesized and purified.

These three probe sequences are blended, and are conjugated to the surface of the well of a microtiter plate, using any one of a variety of standard chemical linkages.

Two PCR primer sequences are selected for each of three targets. These primers are chosen such that each pair will specifically amplify a portion of the target DNA sequence containing the region complementary to the three DNA probes. The 5' end of each of the first pair of primers is labeled with a semiconductor nanocrystal with peak emission at 525 nm. The 5' end of each of the second pair of primers is labeled with a semiconductor nanocrystal with peak emission at 580 nm. The 5' end of each of the third pair of primers is labeled with a semiconductor nanocrystal with peak emission at 650 nm.

These three primer pairs are blended, and are used to simultaneously amplify three defined portions of the target DNA in a standard PCR reaction. Since each of the three semiconductor nanocrystal types are conjugated to their respective primers, and the primers are extended to become the amplified target, each of the three amplified target sequences are labeled with the semiconductor nanocrystal color with which their respective primers were labeled.

After the thermal cycling the amplified target can be denatured or made single-stranded by heating for two minutes at 95° C.

The hybridization is performed by adding 20 μl of the amplified target and 480 μl of 5xSSPE Buffer to the microtiter well coated with three different sequences of DNA probe, and incubating for 60 minutes at 37° C. After hybridization, a wash step under stringent conditions is performed by adding 500 μl of 3xSSPE, and incubating for 15 minutes at 37° C. The well is rinsed twice with water.

The well is scanned in a fluorimeter. UV light is shone upon the well, and the amount of phosphorescence at 525, 580 and 650 nm wavelengths is measured. The presence of 525 nm emission indicates that the immobilized probe captured the first semiconductor nanocrystal labeled amplified target, and remained hybridized after the stringent wash and water rinse steps. The presence of 580 nm emission indicates that the immobilized probe captured the second semiconductor nanocrystal-labeled amplified target. The presence of 650 nm emission indicates that the immobilized probe captured the third semiconductor nanocrystal-labeled amplified target.

This multiplex assay allows simultaneous amplification, labeling and detection of three different targets.

EXAMPLE 15

Sequence-specific Extension

Sequence-specific extension assays are a convenient method for determining the presence or absence of a specific DNA sequence in a sample. Two PCR primers are chosen, and the region of interest such as the site of a Single Nucleotide Polymorphism (SNP) is PCR-amplified. A sequence-specific extension primer is chosen, such that the 3' end of the primer either ends immediately over the site of the SNP, or is within 5 nucleotides of the SNP. This primer is conjugated via its 5' end to a surface, such as a microtiter plate well or bead. In the absence of complete sequence complementarity, the base mismatch will disrupt the double-stranded complex formed by the sequence-specific extension primer and the PCR amplified target. The DNA polymerase has no site for attachment, so extension will not occur. If the primer and amplified target sequences are complementary, sequence-specific extension will occur. If the extension reaction mixture includes a labeled dNTP(e.g., semiconductor nanocrystal-labeled dGTP), the presence or absence of extension can be detected. This allows a determination of the original target sequence.

Two different DNA sequence specific primer sequences are chosen, such that the 3' end of the primers overlaps a SNP in the target DNA sequence by 2 nucleotides. These sequence can range from 15 to 25 nucleotides in length. The first sequence will be completely complementary to allele A, and will be called primer A. The second sequence will be completely complementary to allele B, and will be called primer B.

Primer A and Primer B sequences are chemically synthesized and purified. The 5' end of primer A is conjugated to the surface of the well of a microtiter plate, using any one of a variety of standard chemical linkages.

The 5' end of this primer B is conjugated to the surface of a second well of a microtiter plate, using any one of a variety of standard chemical linkages. A semiconductor nanocrystal-dGTP conjugate is prepared and purified. The semiconductor nanocrystal is chosen with 525 nm emission. Two PCR primer sequences are selected, such that they specifically amplify a portion of the target DNA sequence containing the SNP to be evaluated. These two primers are used to amplify a defined portion of the target DNA in a standard PCR reaction(AmpliTaq Polymerase, dNTPs, Magnesium Chloride, buffer and target DNA).

The sequence-specific extension is performed by combining 2.5 U AmpliTaq DNA polymerase, 2.5 mM magnesium chloride, buffer, 200 $\mu$M dATP, 200 $\mu$M dTTP, 200 $\mu$M dCTP, 20 $\mu$M dGTP, and 200 $\mu$M semiconductor nanocrystal-dGTP conjugate. 95 $\mu$l of this solution is added to the microtiter well coated with sequence-specific primer.

After the thermal cycling, the target is denatured or made single-stranded by heating for two minutes at 95° C. Add 5 $\mu$l of denatured target to the 95 $\mu$l of reaction solution contained in the wells of the microtiter plate. The extension reaction is allowed to occur for 5 minutes at 60° C.

After extension, a wash step under denaturing conditions is performed by adding 500 $\mu$l of 3×SSPE, and incubating for 5 minutes at 95° C. Rinse the well twice with water.

In places where the amplified DNA target annealed to the immobilized primer and extended, the semiconductor nanocrystal with 525 emission is incorporated into the extension sequence, and is thus connected to the surface of the plate via the sequence-specific hybridization. The well is scanned in a fluorimeter. UV light is shone upon the well, and the amount of phosphorescence at 525 nm is measured.

The presence of 525 nm emission indicates that the immobilized probe captured semiconductor nanocrystal-labeled amplified target, and remained hybridized after the stringent wash and water rinse steps.

EXAMPLE 16

Oligonucleotide Ligation Assay

Two oligonucleotide probes are hybridized to adjacent sequences of PCR amplified target DNA with the join situated at the position of a known mutation site. DNA ligase covalently joins the two oligonucleotide probes only if they are perfectly hybridized, which will occur if no mutation is present. Initial studies tagged one probe with biotin and the other with a reporter molecule such as digoxygenin. On transfer to streptavidin-coated microtiter plates washing will remove the reporter labeled probe unless ligation has occurred. Signal detection will therefore only occur if the mutation is not present. This technology was improved by a method of typing two alleles in a single microtiter well, by marking each of the allele-specific primers with different enzyme reporter molecules so that two different colors can be produced. Advances to the ligation technique have replaced the biotin with mobility modifying tails and digoxygenin with fluorescent tags (e.g., FAM, HEX or TET) with the ligation products being electrophoresed and analyzed on an automated sequencer. These modifications have allowed the number of known point mutation sites which can be screened at any one time to be increased.

An oligonucleotide sequence complementary to the wild type of the target sequence is chosen. The 3' end of this oligo ends with the last nucleotide over a Single Nucleotide Polymorphism (SNP). This sequence can range from 15 to 25 nucleotides in length.

A second oligonucleotide sequence is chosen, which is complementary to the mutant sequence of the same SNP. The 3' end of this oligo also ends with the last nucleotide over the SNP site. This sequence can range from 15 to 25 nucleotides in length.

These two DNA probe sequences are chemically synthesized and purified. These oligo probes are separately conjugated by their 5' end to the surface of the wells of a microtiter plate, using any one of a variety of standard chemical linkages.

A single ligation probe sequence is selected. The 5' end of this probe will be directly adjacent to the 3' end of the two selected oligonucleotide sequences. This sequence can range from 10 to 25 nucleotides in length.

The ligation probe is chemically synthesized, and the 5' end is phosphorylated. The 3' end of the ligation probe is conjugated to a semiconductor nanocrystal with emission at 525 nm.

A ligase reaction is performed in each of the two wells containing the two sequences of oligonucleotides. This reaction consists of the ligation probe, denatured or single-stranded target DNA, T7 ligase, magnesium chloride and buffer in an aqueous solution.

The plate can be thermally cycled 25 times from 60° C. to 95° C., with a dwell time of 1 minute at each temperature to achieve arithmetic amplification of the target.

In the presence of the complementary target sequence, the target acts as a template for the ligase reaction. The sequence-specific oligonucleotide and the ligation probe both anneal to the single-stranded target DNA. The T7 enzyme ligates the 3' end of the sequence-specific oligo to the phosphorylated 5' end of the ligation probe.

In the case where the template DNA is not complementary to the sequence-specific oligonucleotide, the mismatch at the 3' end of the annealed specific oligo is sufficient to prevent the ligation reaction.

The wells of the microtiter plate are washed 3 times with water.

In wells where the DNA ligation reaction occurred, the semiconductor nanocrystal with 525 nm emission will be immobilized to the bottom of the well. The well is scanned in a fluorimeter. UV light is shone upon the well, and the amount of phosphorescence at 525 nm is measured.

The presence of 525 nm emission indicates that the ligation probe/semiconductor nanocrystal-conjugate was immobilized to the surface of the well via the ligation reaction, and remained after the water rinse steps.

EXAMPLE 17

Tissue Microarrays for High-Throughput Immunohistochemical Staining of Tumor Specimens Tissue microarrays were prepared as described in Kononen et al. (1998) Nat. Med. 4:844–847. The tumor microarray block was cut into 3–8 μm sections, deparaffinized and prepared for immunochemistry by using conventional techniques. Monoclonal antibody from mouse to cytokeratin 8/18 was used to bind the cytokeratin inside the cells. The excess antibody was removed, the specimen was incubated with biotinylated anti-mouse IgG followed by 40 nM semiconductor nanocrystal-streptavidin. The excess semiconductor nanocrystal-streptavidin was removed and the slides examined under a fluorescence microscope.

The staining pattern of the cells was readily visualized using a fluorescence microscope.

EXAMPLE 18

Use of Semiconductor Nanocrystals in Histochemical and Cytochemical Analyses As explained above, semiconductor nanocrystals may be used to do multiple analysis staining on a tissue sample or blood sample or any sample requiring multiplexed analysis of cellular or extracellular markers. The procedure is carried out in a two-step reaction whereby a primary antibody is followed by a semiconductor nanocrystal-conjugated antibody or by using an antibody (or other biomolecule) semiconductor nanocrystal conjugate to directly label the sample. For example five or more different populations of semiconductor nanocrystals are synthesized with emission spectra that spaced at 40 nm intervals from 490–650 nm. Each spectrally distinct population of semiconductor nanocrystal is conjugated to a different molecule which specifically recognizes the biomolecule of interest which may or may not be present in the sample to be analyzed. Following standard staining protocols, the sample is labeled with the semiconductor nanocrystals and analyzed for the location and quantity of the target molecule.

A. The sample is prepared for immunohistochemical analysis. The incubation buffer is PBS+0.1% BSA+NaN$_3$ (or similar buffer). Active groups are blocked. The sample is washed and incubated with semiconductor nanocrystal conjugates (the number dependent on the number of parameters being assessed). The sample is then washed, mounted and analyzed using conventional fluorescent microscopy techniques or a spectral scanning device as described above.

B. Cellular compounds that are known to exist in spatially distinct regions of a cell are labeled with the same six colors. In this case, six different compounds can be unambiguously monitored in each distinct location within the cell.

C. Compounds in spatially distinct regions of the cell are labeled with different sets of 6 colors, where each set has a small wavelength shift relative to the others. For instance, proteins located in the nucleus are labeled with semiconductor nanocrystals that emit at 500, 530, 560, 590, 620 and 650 nm, while proteins located in the cellular membrane are labeled with 505, 535, 565, 595, 625 and 655 nm emitting semiconductor nanocrystals. The advantage to using nonidentical sets of colors is that if the location of compounds is not known, this type of "barcoding" of the different cellular compounds can be used to unambiguously determine the location of each. A problem arises only when nonspectrally distinct semiconductor nanocrystals (e.g. 550 and 555) colocalize. If this happens, however, the information can be used in a second experiment where the labels on the colocalized compounds are rearranged to eliminate the spectral overlap. For instance, in the example of colocalized 550 and 555 nm emitting semiconductor nanocrystals, the 555 nm label is replaced in a second experiment with 590 nm emitting semiconductor nanocrystals. By barcoding different cellular compounds, it may be possible with CdSe semiconductor nanocrystals to track the location of as many as 150 distinct compounds within a cell. Using other semiconductor nanocrystal materials such as CdTe, InP, InAs, CdS, etc. can dramatically increase this number.

EXAMPLE 19

Competitive Microsphere Filter Assay

An explained above, semiconductor nanocrystals can be used in competitive microsphere filter assays, such as competitive latex immunoassays. In this application the detection agent is a semiconductor nanocrystal or a semiconductor nanocrystal-encoded solid conjugate. The conjugate is a molecule that specifically recognizes the analyte. The antigen conjugates are direct semiconductor nanocrystal-antigen conjugates or semiconductor nanocrystal-dyed microsphere-conjugates that are small enough to pass through filter pores.

This allows multiple simultaneous detections using a light source for excitation of the semiconductor nanocrystals and detection of emissions. The detection takes place on the filter or in the filtrate and the assay may be carried out in a high throughput multiwell environment. The filters in this format are opaque to the excitation light and allow detection of semiconductor nanocrystals in the filtrate without the need for washes or sample removal.

In particular, antibodies to a specific analyte are immobilized on microspheres with a diameter greater than that of the filter pores using standard adsorption or conjugation technologies. The antibody conjugates are placed in an appropriate buffer (e.g. PBS) in the upper chamber or insert in a 96-well plate separated from the bottom of the plate by a light impermeant porous filter (e.g. BD fluoblock filters). The medium containing the analyte(s) and a standard amount of analyte(s) labeled with semiconductor nanocrystals that have a diameter less than that of the filter pores are added to the upper chamber or insert. After an appropriate incubation time (e.g., 30 seconds to 24 hours) the amount of fluorescence in the lower chamber is quantitated by spectral analysis systems described above.

This assay provides information on the concentration of analyte(s) in any biological medium. It is especially useful for measuring multiple analytes in a diagnostic type test and may also be used for environmental, research or screening applications. The greater the concentration of analyte in the sample the greater the amount of fluorescence detected in the lower chamber. Thus, this system provides a desirable increasing curve in terms of analyte concentration.

Figure 5:
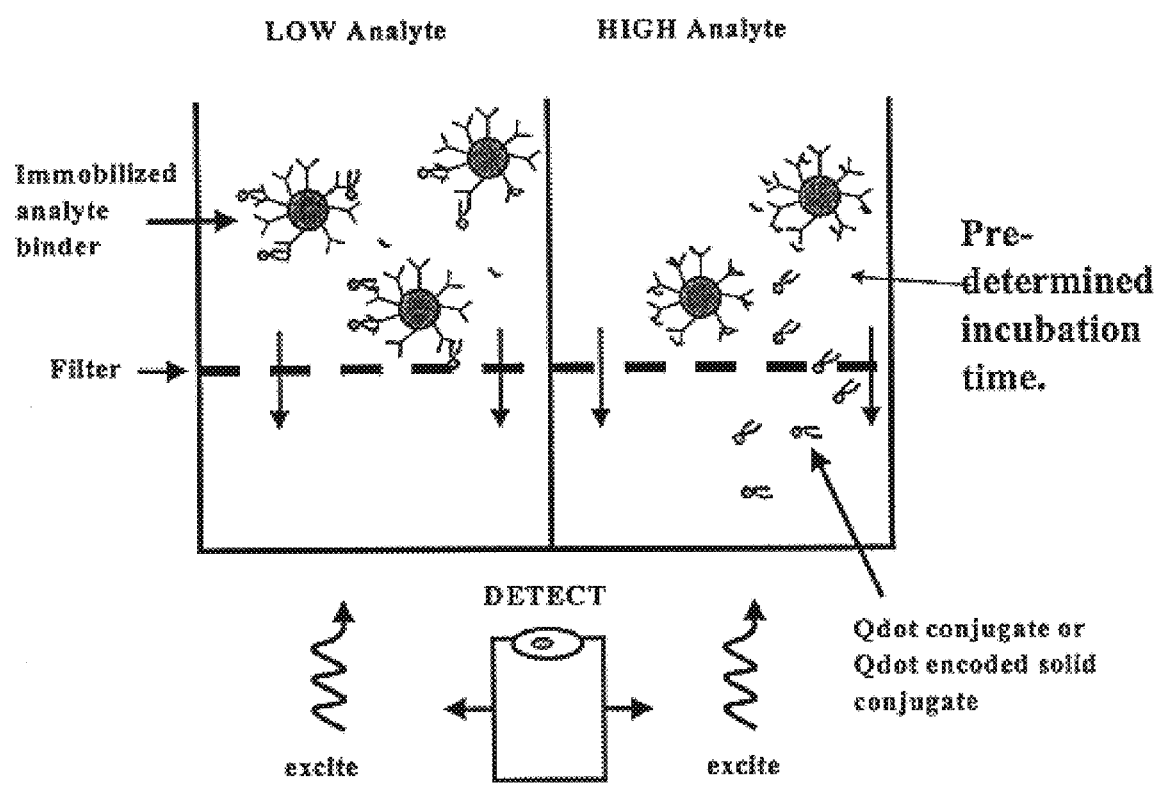
FIG. 5 is a pictorial representation of a competitive microsphere filter assay as described in Example 19.

FIG. 5 is a pictorial representation of a competitive microsphere filter assay as described herein.

Thus, novel methods for using semiconductor nanocrystals are disclosed. Although preferred embodiments of the subject invention have been described in some detail, it is understood that obvious variations can be made without departing from the spirit and the scope of the invention as defined by the appended claims.

We claim:

1. A method of detecting a target polynucleotide analyte in a sample containing or suspected of containing the polynucleotide analyte, comprising the steps of:

(a) providing the sample on a solid support;
(b) combining with said sample a specific-binding molecule, wherein (i) said specific-binding molecule comprises a first member of a binding pair, (ii) the specific-binding molecule is a polymerase chain reaction (PCR) amplification product, which product comprises said first member of the binding pair, and (iii) said combining is performed under conditions that allow formation of a first complex comprising said specific-binding molecule and said polynucleotide analyte, when present;
(c) removing any unbound specific-binding molecule;
(d) combining said first complex with a second member of the binding pair, wherein (i) said second member of the binding pair is linked to a first semiconductor nanocrystal; and (ii) said combining is performed under conditions that allow formation of a second complex comprising the first complex and the second member of the binding pair; and
(e) detecting the presence of the second complex, if present, by monitoring a spectral emission mediated by the first semiconductor nanocrystal in the second complex, wherein the emission indicates the presence of polynucleotide analyte in the sample.

2. The method of claim 1, wherein the polynucleotide analyte is contained within a chromosome or chromosomal fragment.

3. The method of claim 1, wherein the polynucleotide analyte is a DNA molecule.

4. The method of claim 1, wherein the polynucleotide analyte is an RNA molecule.

5. The method of claim 1, wherein the specific-binding molecule is an aptamer.

6. The method of claim 1, wherein the first member of the binding pair is biotin and the second member of the binding pair is avidin or streptavidin.

7. The method of claim 1, wherein the first member of the binding pair is digoxygenin and the second member of the binding pair is an antibody directed against digoxygenin.

8. The method of claim 1, wherein the first member of the binding pair is flourescein and the second member of the binding pair is an antibody directed against flourescein.

9. The method of claim 1, wherein there is a second target polynucloetide analyte, wherein the method further comprises:
    combining with said sample a second specific-binding molecule, wherein (i) said second specific-binding molecule comprises a first member of a second binding pair, (ii) the second specific-binding molecule is a second polymerase chain reaction (PCR) amplification product, which second amplification product comprises the first member of the second binding pair, and (iii) said combining is performed under conditions that allow formation of a third complex comprising said second specific-binding molecule and said second polynucleotide analyte, when the second target analyte is present;
    removing any unbound second specific-binding molecule;
    combining said third complex with a second member of the second binding pair, wherein (i) said second member of the second binding pair is linked to a second semiconductor nanocrystal that has a second emission spectrum distinct from that of the first semiconductor nanocrystal; and (ii) said combining is performed under conditions that allow formation of a fourth complex comprising the third complex and the second member of the second binding pair; and
    detecting the presence of the fourth complex, if present, by monitoring the second spectral emission mediated by the second semiconductor nanocrystal in the fourth complex, wherein the second emission indicates the presence of the second target polynucleotide analyte in the sample.

10. The method of claim 1, wherein the first member of the binding pair is selected from the group consisting of a polynucleotide, a hapten and a biotin.

11. The method of claim 1, wherein the second member of the binding pair is selected from the group consisting of a polynucleotide, an anti-hapten, avidin, and a streptavidin.

12. The method of claim 1, wherein the first member of the binding pair is a hapten and the second member of the binding pair is an anti-hapten.

13. The method of claim 12, wherein the hapten is digoxigenin, fluorescein, dinitrophenol, bromodeoxyuridine, and mouse immunoglobulin and the antihapten is anti-digoxigenin, anti-fluorescein, anti-dinitrophenol, anti-bromodeoxyuridine, and anti-mouse immunoglobulin, respectively.

14. The method of claim 1, wherein the first and second members of the binding pair are complementary polynucleotide molecules capable of forming nucleic acid duplex.

15. The method of claim 1, wherein the sample is a sample of isolated cells, a tissue sample, or a fluid sample.

16. The method of claim 1, wherein there is a second analyte, wherein the method further comprises:
    combining with said sample a second specific-binding molecule, wherein (i) said second specific-binding molecule comprises a first member of a second binding pair, and (ii) said combining is performed under conditions that allow formation of a third complex comprising said second specific-binding molecule and said second analyte when said second analyte, is present;
    removing any unbound second specific-binding molecule;
    combining said third complex with a second member of the second binding pair, wherein (i) said second member of the second binding pair is linked to a second semiconductor nanocrystal that has a second emission spectrum distinct from that of the first semiconductor nanocrystal; and (ii) said combining is performed under conditions that allow formation of a fourth complex comprising said third complex and the second member of the second binding pair; and
    detecting the presence of the fourth complex, if present, by monitoring the second spectral emission mediated by the second semiconductor nanocrystal in the fourth complex, wherein the second emission indicates the presence of the second target analyte in the sample.

17. The method of claim 16, wherein the second target analyte is a polypeptide analyte.

18. The method of claim 16, wherein the second specific-binding molecule is a polypeptide specific-binding molecule.

19. The method of claim 18, wherein the polypeptide specific-binding molecule is an antibody.

20. The method of claim 1, wherein the specific-binding molecule comprises a plurality of first members of binding pairs, which first members may be the same or different.

21. The method of claim 20, wherein the plurality of first members are the same.

22. The method of claim 1, wherein the PCR is reverse transcriptase-PCR (RT-PCR).

23. The method of claim 9, wherein the PCR is reverse transcriptase-PCR (RT-PCR).

24. The method of claim 9, wherein the first member of the second binding pair is selected from the group consisting of a polynucleotide, a hapten and a biotin.

25. The method of claim 9, wherein the second member of the second binding pair is selected from the group consisting of a polynucleotide, an anti-hapten, an avidin, and a streptavidin.

26. The method of claim 9, wherein the first member of the second binding pair is a biotin and the second member of the second binding pair is avidin or streptavidin.

27. The method of claim 9, wherein the first member of the second binding pair is a hapten and the second member of the second binding pair is an anti-hapten.

28. The method of claim 27, wherein the hapten is digoxigenin, fluorescein, dinitrophenol, bromodeoxyuridine, and mouse immunoglobulin and the antihapten is anti-digoxigenin, anti-fluorescein, anti-dinitrophenol, anti-bromodeoxyuridine, and anti-mouse immunoglobulin, respectively.

29. The method of claim 9, wherein the first and second members of the second binding pair are complementary polynucleotide molecules capable of forming nucleic acid duplex.

30. The method of claim 9, wherein the second specific-binding molecule is an aptamer.

31. The method of claim 9, wherein the sample is a sample of isolated cells, a tissue sample, or a fluid sample.

32. The method of claim 9, wherein the polynucleotide target analytes are present on more than one chromosome or more than one chromosome fragment.

33. The method of claim 9, wherein the polynucleotide target analytes are present on the same chromosome or chromosome fragment.

34. The method of claim 9, wherein each of the polynucleotide target analytes is a DNA molecule.

35. The method of claim 9, wherein each of the polynucleotide target analytes is an RNA molecule.

36. The method of claim 9, wherein the polynucleotide target analytes are a combination of DNA molecules and RNA molecules.

37. The method of claim 9, wherein each specific-binding molecule comprises a plurality of first members of binding pairs, which first members may be the same or different.

38. The method of claim 37, wherein on each specific-binding molecule the plurality of first members are the same.

39. The method of claim 16, wherein each specific-binding molecule comprises a plurality of first members of binding pairs, which first members may be the same or different.

40. The method of claim 39, wherein on each specific-binding molecule the plurality of first members are the same.

* * * * *